(12) United States Patent
Carr et al.

(10) Patent No.: US 11,878,160 B2
(45) Date of Patent: Jan. 23, 2024

(54) NEUROMODULATION DEVICE

(71) Applicant: GALVANI BIOELECTRONICS LIMITED, Middlesex (GB)

(72) Inventors: Michael John Carr, King of Prussia, PA (US); Kevin K. Kwong, King of Prussia, PA (US); Gerald E. Hunsberger, King of Prussia, PA (US)

(73) Assignee: Galvani Bioelectronics Limited, Middlesex (GB)

( * ) Notice: Subject to any disclaimer, the term of this patent is extended or adjusted under 35 U.S.C. 154(b) by 220 days.

(21) Appl. No.: 15/752,502

(22) PCT Filed: Aug. 18, 2016

(86) PCT No.: PCT/IB2016/054957
§ 371 (c)(1),
(2) Date: Feb. 13, 2018

(87) PCT Pub. No.: WO2017/033101
PCT Pub. Date: Mar. 2, 2017

(65) Prior Publication Data
US 2018/0236224 A1    Aug. 23, 2018

Related U.S. Application Data

(60) Provisional application No. 62/208,057, filed on Aug. 21, 2015.

(51) Int. Cl.
*A61N 1/20* (2006.01)
*A61N 1/36* (2006.01)
(Continued)

(52) U.S. Cl.
CPC .............. *A61N 1/205* (2013.01); *A61B 5/087* (2013.01); *A61B 5/0816* (2013.01); *A61B 5/091* (2013.01);
(Continued)

(58) Field of Classification Search
CPC ................ A61N 1/205; A61N 1/36053; A61N 1/36057; A61N 1/3611; A61N 1/36171;
(Continued)

(56) References Cited

U.S. PATENT DOCUMENTS 8,088,127 B2 * 1/2012 Mayse ............... A61B 18/1477
606/41
8,483,831 B1  7/2013 Hlavka et al.
(Continued)

FOREIGN PATENT DOCUMENTS

WO    WO 93/02744    2/1993

*Primary Examiner* — Tammie K Marlen
(74) *Attorney, Agent, or Firm* — Banner & Witcoff, Ltd.

(57) ABSTRACT

The present invention provides devices and methods that can prevent or ameliorate bronchoconstriction by stimulating neural activity, in contrast to those techniques based on denervation, ablation or blocking of neural activity. Methods and devices according to the invention may act responsively or on demand, can preserve neuronal structure and function and will be associated with minimal collateral side-effects. In particular, the invention provides devices and methods in which a signal is delivered to the vagus nerve, for example the cervical vagus nerve or the pulmonary branch of the vagus nerve, in order to stimulate neural activity in the vagal nerve.

15 Claims, 12 Drawing Sheets

Figure 1:
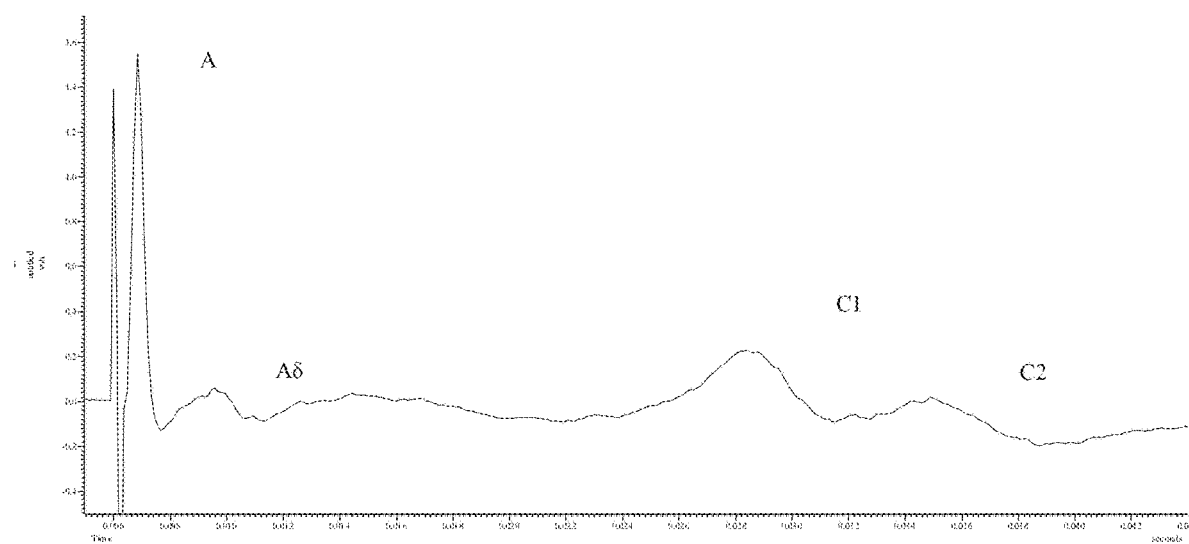

(51) Int. Cl.
    *A61B 5/388*    (2021.01)
    *A61B 5/08*     (2006.01)
    *A61B 5/087*    (2006.01)
    *A61B 5/091*    (2006.01)
    *A61B 5/145*    (2006.01)
    *A61B 5/00*     (2006.01)

(52) U.S. Cl.
    CPC .......... *A61B 5/14542* (2013.01); *A61B 5/388* (2021.01); *A61B 5/4035* (2013.01); *A61B 5/4836* (2013.01); *A61N 1/3611* (2013.01); *A61N 1/36053* (2013.01); *A61N 1/36057* (2013.01); *A61N 1/36171* (2013.01); *A61B 5/08* (2013.01)

(58) Field of Classification Search
    CPC ... A61B 5/04001; A61B 5/0816; A61B 5/087; A61B 5/091; A61B 5/14542; A61B 5/4035; A61B 5/4836; A61B 5/08; A61B 5/24

See application file for complete search history.

(56)            References Cited

U.S. PATENT DOCUMENTS

| | | |
|---|---|---|
| 2007/0027496 A1   | 2/2007  | Parnis et al. |
| 2009/0187231 A1*  | 7/2009  | Errico .................. A61N 1/3611 607/42 |
| 2010/0217347 A1   | 8/2010  | Swoyer et al. |
| 2012/0302909 A1*  | 11/2012 | Mayse .................. A61B 5/087 600/532 |
| 2013/0238050 A1*  | 9/2013  | Simon .................... A61N 2/006 607/42 |
| 2014/0186341 A1   | 7/2014  | Mayse |
| 2015/0202437 A1   | 7/2015  | Franke et al. |

* cited by examiner

A

B

A

B

A

B

A

B

NEUROMODULATION DEVICE

This application is filed pursuant to 35 U.S.C. § 371 as a United States National Phase Application of International Patent Application Serial No. PCT/IB2016/054957 filed Aug. 18, 2016, which claims priority to United States Provisional Application No. U.S. 62/208,057 filed Aug. 21, 2015, and the entire contents of each of the foregoing applications are hereby incorporated by reference.

The passage of air into the lungs occurs via conducting airways whose calibre is not constant but can be modulated by changes in tone of the airway smooth muscle (ASM) located in the walls of the conducting airways. The degree of tone is largely under the control of the parasympathetic nerves that release acetylcholine to cause contraction. A degree of tone is present under resting conditions such that drugs that block the interaction of acetylcholine on airway smooth muscle cause a relaxation of the muscle and hence increase the calibre of the airways resulting in a lower resistance to airflow. This bronchodilation is of benefit in patients with airway disease such as Asthma and Chronic Obstructive Pulmonary Disease (COPD).

Small molecule "bronchodilators" reverse contraction of the airway smooth muscle either by acting as agonists for sympathetic neurotransmitters (e.g. catecholamines such as nor-epinephrine and epinephrine), or by acting as antagonists for parasympathetic neurotransmitters. For example, beta-adrenoceptor agonists (e.g. salbutamol) act as bronchodilators by activating beta 2 adrenoceptors in airway smooth muscle, which, when activated, cause relaxation of airway smooth muscle. Antimuscarinic bronchodilators (also known as anticholinergics) act by blocking muscarinic receptors in the airway smooth muscle that would otherwise cause bronchoconstriction when activated via acetylcholine-mediated parasympathetic signalling.

Modifying the balance between bronchodilatory and bronchoconstrictive signalling has formed the basis for a number of treatments of diseases characterised by bronchoconstriction, such as asthma and COPD. In the early $20^{th}$ century, denervation—severing the nerves that innervate the lung—was investigated as a therapeutic approach to these diseases. However, such methods were crude and resulted in significant side-effects, likely because the vagus nerve controls numerous organs and body functions besides the lungs and respiration. Modern attempts to influence the balance of neural signalling through destructive processes such as partial or whole ablation of the nerves may have similar drawbacks.

The level of activity of parasympathetic nerves that innervate the airways can be increased or decreased by inputs from three distinct subsets of sensory nerves carried in the vagus nerve whose sensory endings are located in the conducting airways and lungs (Coleridge H M, Coleridge J C. Annu Rev Physiol. 1994; 56:69-91, incorporated herein by reference). Two sensory nerve subtypes whose activation is associated with increased activity in parasympathetic nerves are selectively activated by irritants and are known as Rapidly Adapting Receptors (RARs) and C-fibres. RAR and/or C-fibre activation is associated with bronchoconstriction. In contrast Slowly Adapting Receptors (SARs) are not activated by irritants but are activated by stretch of the airways during lung inflation. It is generally accepted that an increase in the activity from SARs accompanying inspiration exerts an inspiration-inhibiting influence on breathing by terminating inspiration and promoting expiration. This is known as the Hering-Breuer reflex. This reflex is present in conscious and anesthetized animals, and can be demonstrated in human infants (Hassan A, Gossage J, Ingram D, Lee S, Milner A D. J Appl Physiol. 2001; 90:763-769, which is incorporated herein by reference); however, it does not play a role in modulation of breathing in adult humans, despite clear evidence of SAR activity (Guz A, Trenchard D W. J Physiol. 1971 March; 213(2):329-43, which is incorporated herein by reference). Lung stretch is also associated with bronchodilation, and is mediated by the SARs responsible for the Hering-Breuer reflex (Widdicombe J G, Nadel J A. J Appl Physiol. 1963 July; 18:681-6, which is incorporated herein by reference). Unlike the Hering Breuer reflex, lung stretch-induced bronchodilation is present in healthy humans but is much reduced in lung disease such as asthma (Kapsali T, Permutt S, Laube B, Scichilone N, Togias A. J Appl Physiol (2000); 89(2):711-20, which is incorporated herein by reference) and COPD (Scichilone N, La Sala A, Bellia M, Fallano K, Togias A, Brown R H, Midiri M, Bellia V. J Appl Physiol (2008); 105(3):832-8, which is incorporated herein by reference) suggesting restoration of this reflex bronchodilation by increasing SAR-associated activity may be of clinical benefit.

SARs, in stark contrast to lung C-fibres and RARs, are not known to be selectively sensitive to chemical or pharmacological stimuli. SAR-associated fibres also differ in their electrophysiological properties from RAR-associated fibres and C-fibres; in particular SARs tend to arise from much faster conducting vagal fibres than C-fibres and as a population tend to conduct faster than RARs—although there is overlap between the lower end of the range of SAR conduction velocity and the faster end of RAR conduction velocity. This difference in conduction velocity between the fastest SARs and the majority of RARs and C-fibres is important. All three of these afferent nerve subtypes travel in the vagus; however, SAR-associated fibres are among the fastest conducting fibres.

US2015/0202437 describes use of an electrical signal to cause a "depletion block" in a laryngeal nerve. According to US2015/0202437, the "depletion block" is induced by raising the number of action potentials in a pre-synaptic nerve in order that the nerve can no longer effectively signal to a post-synaptic membrane. The functional effect of the electrical signal is therefore an inhibition (block) of effective neural activity.

SUMMARY OF INVENTION

The present invention provides devices and methods that can prevent or ameliorate bronchoconstriction by stimulating neural activity, in contrast to those techniques based on denervation, ablation or blocking of neural activity. Methods and devices according to the invention may act responsively or on demand, can preserve neuronal structure and function and will be associated with minimal collateral side-effects. In particular, the invention provides devices and methods in which a signal is delivered to the vagus nerve, for example the cervical vagus nerve or the pulmonary branch of the vagus nerve, in order to stimulate neural activity in the vagal nerve.

A particular advantage of the devices and methods of the invention is that the signal applied to the vagus nerve is able to selectively stimulate neural activity in the afferent fibres of the vagal nerve, in preference to vagal efferent fibres. Unwanted cross-stimulation of efferent vagal fibres would likely lead to unintended downstream side-effects. Therefore, selective stimulation is advantageous in allowing the intended therapeutic effect to be induced but reducing unwanted side-effects that may be caused by cross-stimulation of efferent fibres.

A further advantage of the devices and methods of the invention is that the signal applied to the vagus nerve is able to selectively stimulate neural activity in the A fibres of the vagus nerve in preference to the Aδ and C fibres. As shown in FIG. 1, a compound action potential of the vagal nerve comprises three waves: the first wave is indicative of the action potential component carried by A fibres. A-fibres have a high conduction velocity as they are relatively thick and are myelinated. The second wave is indicative of the action potential component carried by Aδ fibres. Aδ fibres are myelinated but have a lower conduction velocity compared to A fibres as Aδ fibres are thinner. The third wave is indicative of the action potential component carried by C fibres. C fibres have a lower conduction velocity than Aδ fibres as they are thin and unmyelinated (Carr Wand Undem B J, Respirology (2003); 8, 291-301, which is incorporated herein by reference in its entirety). As discussed above, SAR-associated signalling is predominantly associated with high conduction velocity fibres (predominantly A fibre neural activity), with RAR-associated fibres having lower conduction velocities (predominantly Aδ fibre neural activity).

By stimulating neural activity in vagal afferent fibres, in particular A fibres, the present invention is able to reduce bronchoconstriction (see Examples). Without wishing to be bound by theory, it is hypothesised that this effect is due to an increase in lung slowly activating receptor (SAR)-associated signalling. By stimulating afferent vagal neural activity, in particular in vagal afferent A fibres, it is hypothesised that the present invention increases SAR-associated signalling, resulting in relaxation of airway smooth muscle (ASM), thereby relieving or preventing bronchoconstriction. Selective stimulation of afferent fibres in preference to efferent fibres has the advantage of reducing unwanted pro-constrictive efferent signalling and downstream side-effects. Selectively stimulating afferent A fibres in preference to afferent Aδ fibres is further advantageous, as selectively stimulating the higher conduction velocity fibres reduces or avoids any contribution of RAR-associated afferent signalling, which is associated with bronchoconstriction. Therefore reducing any increase in neural activity in Aδ fibres versus the activity in afferent A fibres will further increase the SAR-associated bronchodilatory effect.

Therefore, in a first aspect the invention provides an apparatus for stimulating neural activity in a vagal nerve of a patient, the apparatus comprising one or more transducers each configured to apply a signal to said vagal nerve of the patient, and a controller coupled to the one or more transducers, the controller controlling the signal to be applied by each of the one or more transducers, such that the signal stimulates the neural activity of said nerve to produce a physiological response in the patient. In certain embodiments, the signal selectively stimulates neural activity in afferent fibres of the nerve to which the signal is applied, optionally selectively stimulates neural activity in afferent A fibres of the nerve.

In a second aspect, the invention provides a method of treating bronchoconstriction, optionally COPD-associated or asthma-associated bronchoconstriction, in a patient comprising: (i) implanting in the patient an apparatus according to the first aspect; (ii) positioning at least one transducer of the apparatus in signalling contact with a vagal nerve of the patient; and (iii) activating the apparatus.

In a third aspect, the invention provides a method of treating bronchoconstriction, optionally COPD-associated or asthma-associated bronchoconstriction, in a patient, the method comprising applying a signal to a vagal nerve of said patient to stimulate neural activity in said nerve in the patient. In certain embodiments, the signal selectively stimulates neural activity in afferent fibres of the nerve to which the signal is applied, optionally selectively stimulates neural activity in afferent A fibres of the nerve.

In a fourth aspect, the invention provides a bronchodilator for use in a method of treating bronchoconstriction in a patient, wherein the method comprises: (i) applying a signal to a vagal nerve of said patient to stimulate neural activity in said vagal nerve; and (ii) administering the bronchodilator to the patient. In certain embodiments the bronchodilator is an anticholinergic compound or a beta-adrenoreceptor agonist. In certain embodiments, the signal selectively stimulates neural activity in afferent fibres of the nerve to which the signal is applied, optionally selectively stimulates neural activity in afferent A fibres of the nerve.

In a fifth aspect, the invention provides a neuromodulatory electrical waveform for use in treating bronchoconstriction, for example COPD-associated or asthma-associated bronchoconstriction, in a patient, wherein the waveform is a direct current (DC) waveform having a frequency of 1-1000 Hz, such that, when applied to a vagal nerve, of the patient, the waveform stimulates neural signalling in the nerve, optionally selectively stimulating neural activity in the afferent fibres of the nerve, more preferably selectively stimulating neural activity in the afferent A fibres.

In a sixth aspect, the invention provides a use of a neuromodulation device for treating bronchoconstriction, for example COPD-associated or asthma-associated bronchoconstriction, in a patient by stimulating neural activity in a vagal nerve of the patient, optionally selectively stimulating neural activity in the afferent fibres of the vagal nerve, optionally selectively stimulating neural activity in the afferent A fibres of the vagal nerve.

In a seventh aspect, the invention provides a bronchodilator for use in treating bronchoconstriction in a patient, the patient having an apparatus according to the first aspect implanted.

In an eighth aspect, the invention provides a neuromodulation system, the system comprising a plurality of apparatuses according to the first aspect. In such a system, each apparatus may be arranged to communicate with at least one other apparatus, optionally all apparatuses in the system. In certain embodiments, the system is arranged such that, in use, the apparatuses are positioned to bilaterally modulate the neural activity of the afferent fibres of the vagal nerves of a patient.

In a preferred embodiment of all aspects of the invention, the patient is a human.

DETAILED DESCRIPTION

Figures

FIG. 1: Exemplar compound action potential (CAP) trace of Sprague Dawley rat left vagus. Stimulation performed with 300 μm cuff (CorTec), bath warmed to 35° C., approx. 20 mm conduction distance between cathode and initial recording electrode. A, Aδ and C1 and C2 waves are labelled.

Figure 2:
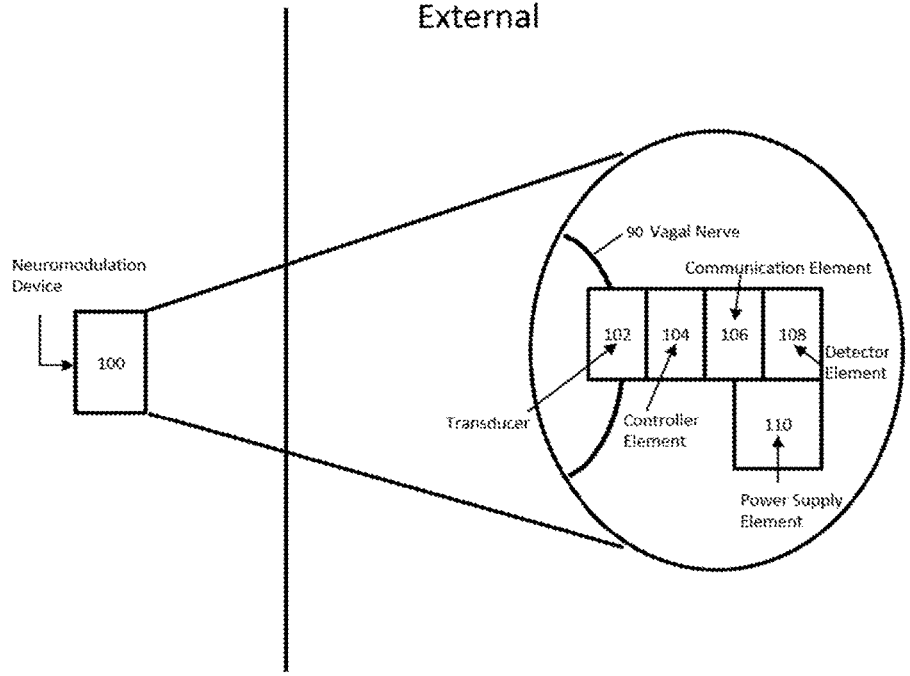
Figure 2:
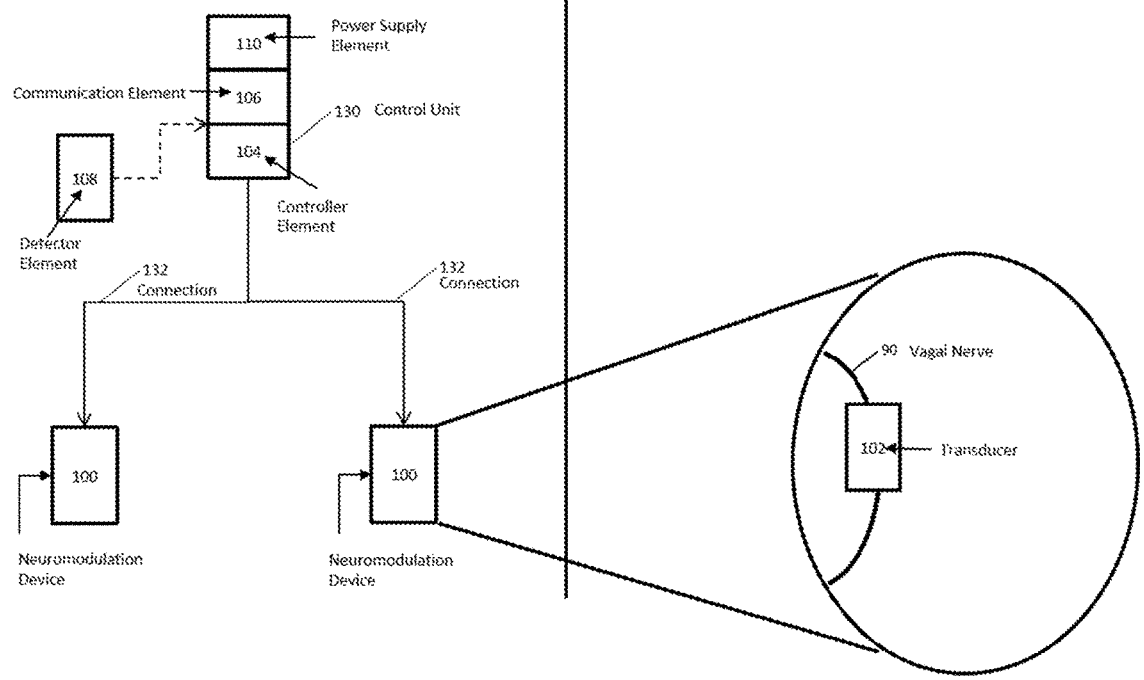
Figure 2C:
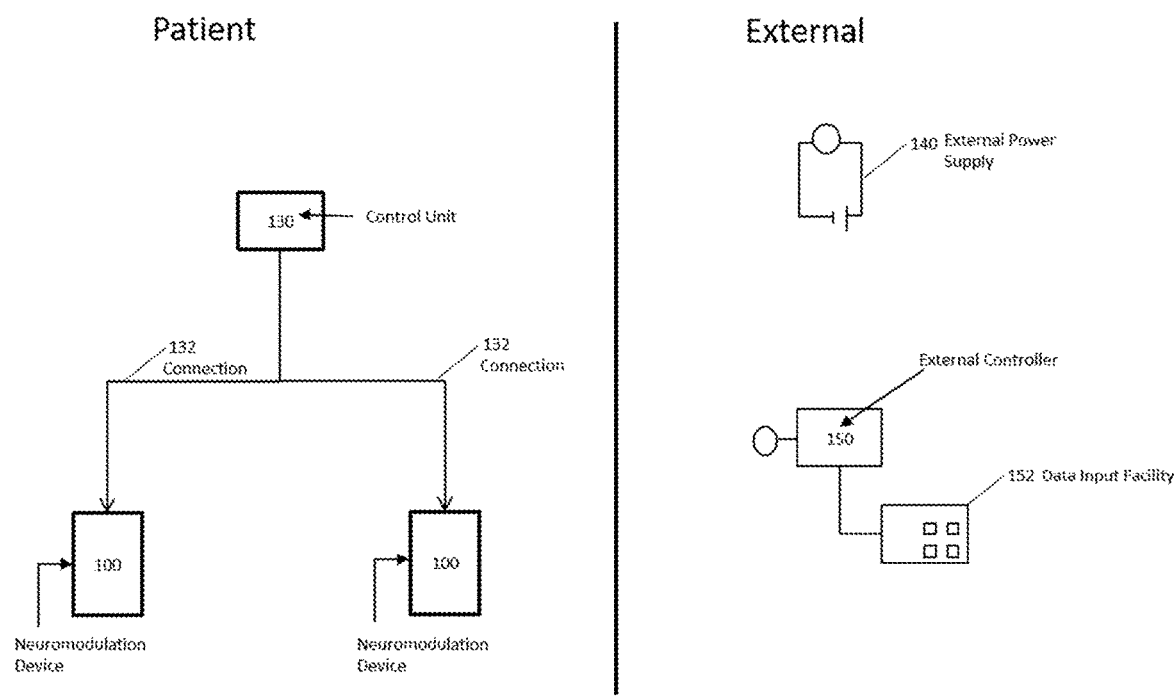

FIG. 2: Schematic drawings showing how apparatuses, devices and methods according to the invention can be put into effect. FIGS. 2A, 2B and 2C illustrate components of a neuromodulation device 100, in which the device comprises several elements and components, a vagal nerve 90, a transducer 102, a controller element 104, a communication element 106, a detector element 108, a power supply element 110, a control unit 130, connections 132, an external power supply 140, an external controller 150 and a data input facility 152.

Figure 3:
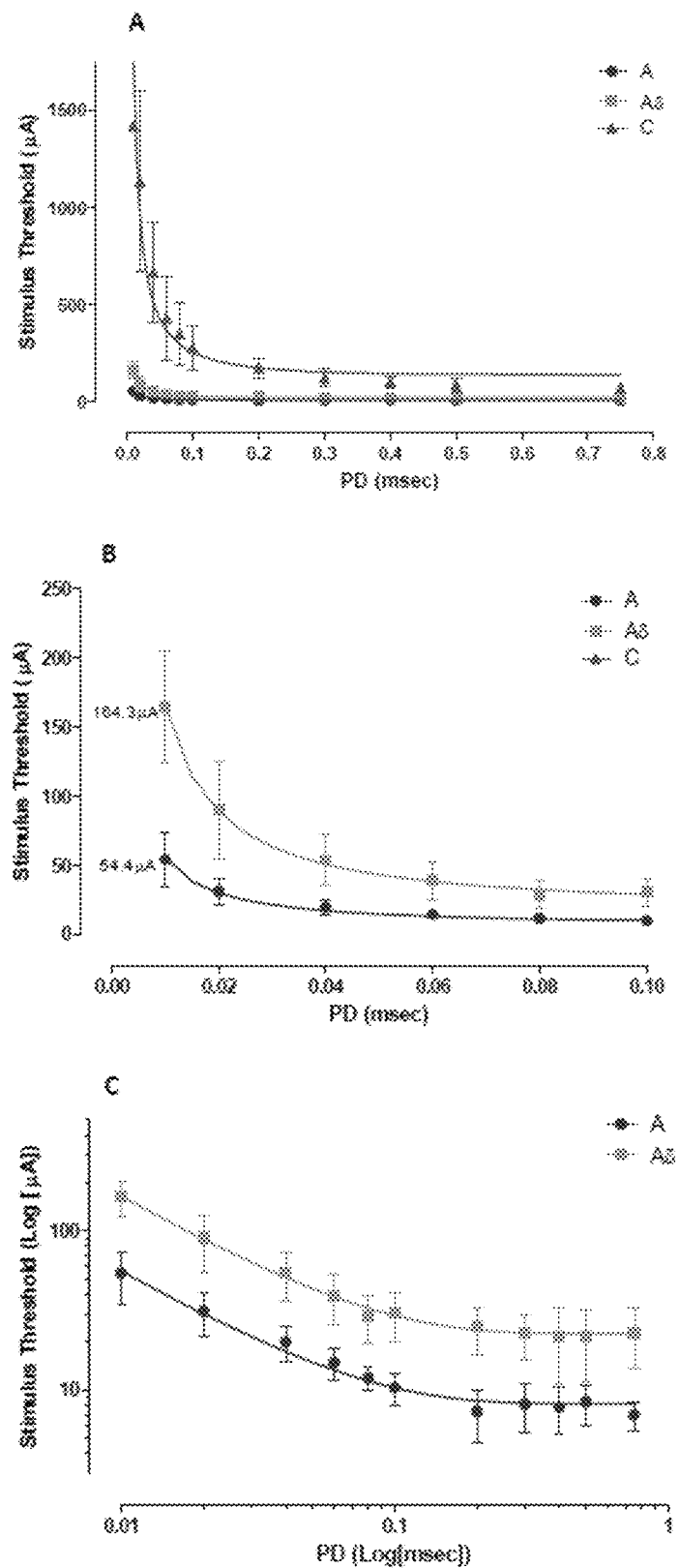

FIG. 3: Strength/duration plots of Sprague Dawley rat left vagus, n=3. Stimulation performed with 300 μm cuff (CorTec), bath warmed to 35° C. A) Full scale. B) Reduced scale. C) Logarithmic ordinate/abscissa scale. A-fibers (circle), Aδ-fibers (square), C-fibres (triangles).

Figure 4:
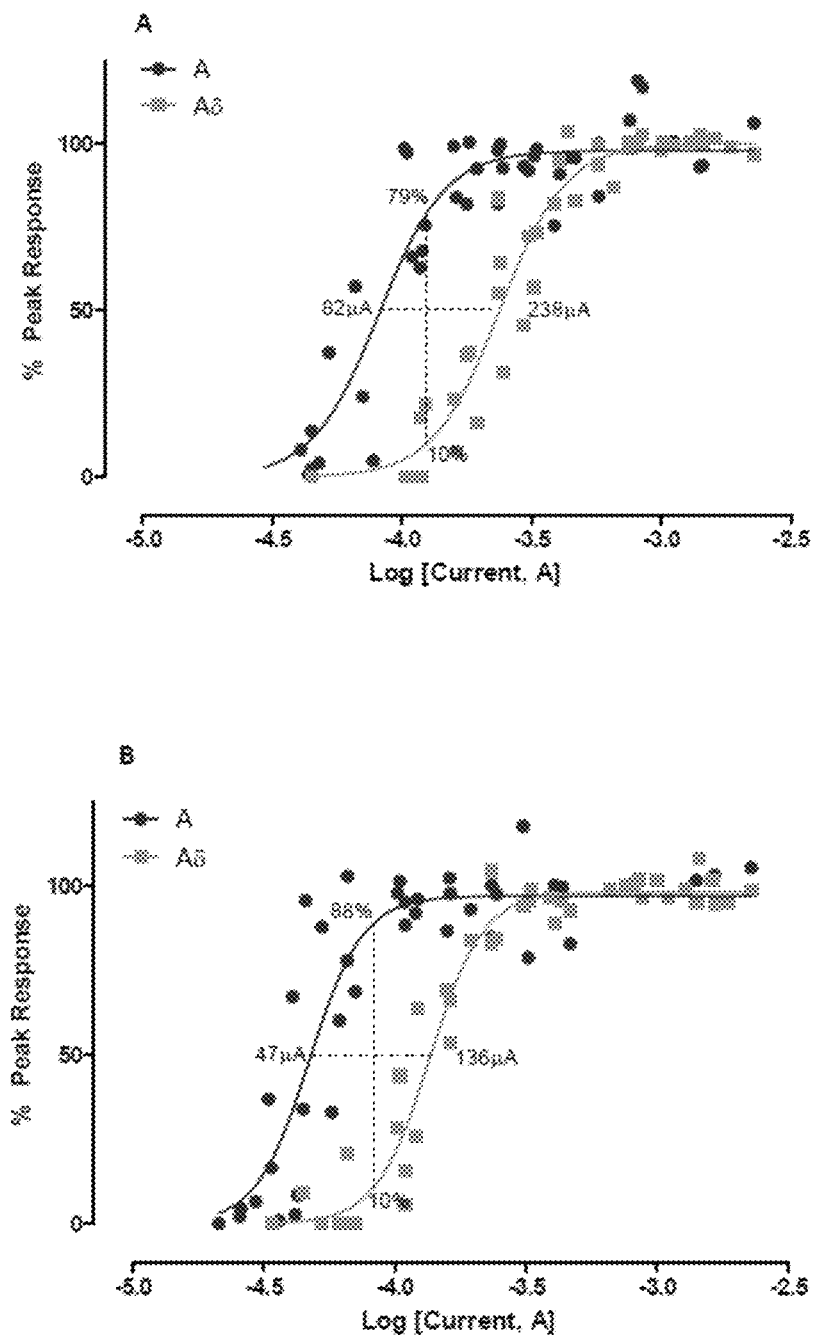

FIG. 4: Logarithmic current response curves of Sprague Dawley rat left vagus A-fibers (circle) and Aδ-fibers (square) with pulse durations of A) 0.01 msec and B) 0.02 msec, n=5. Stimulation performed with 300 μm cuff (CorTec), bath warmed to 35° C.

Figure 5:
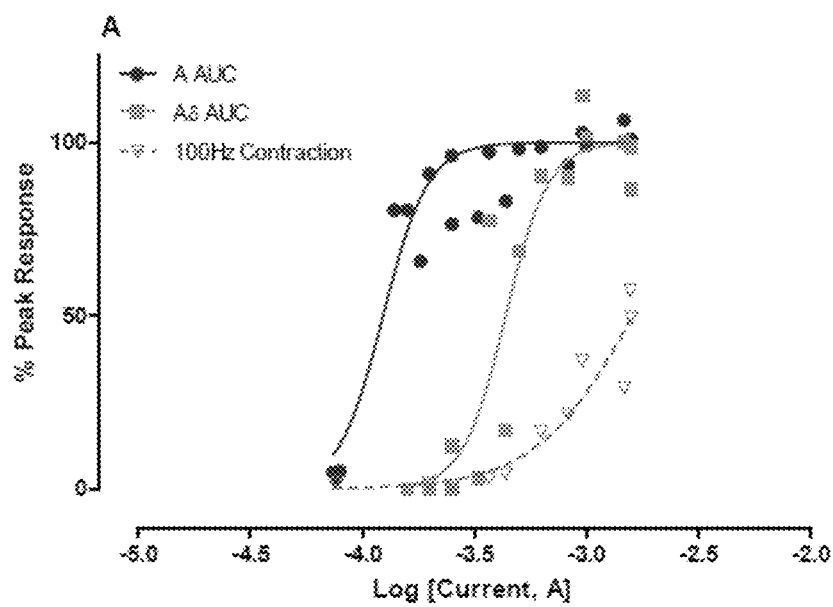
Figure 5:
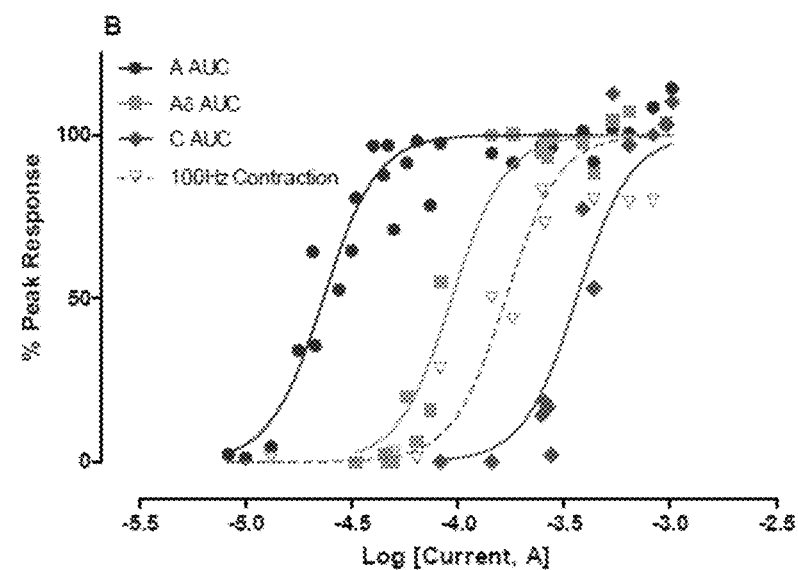

FIG. 5: Paired logarithmic current response curves of Sprague Dawley right vagus A-fibers (circle), Aδ-fibers (square), C-fiber (diamond), and efferent parasympathetic contractions (triangle, 100 Hz in 0.8 Hz, 350 msec trains) with pulse durations of (A) 0.01 msec and (B) 0.2 msec, n=3. Stimulation performed with 300 μm cuff (CorTec), bath perfused at 35° C.

Figure 6:
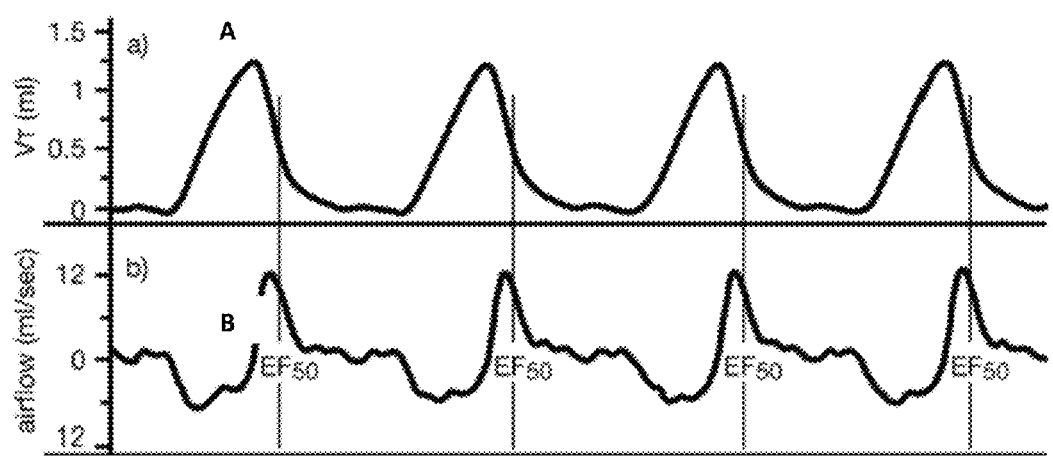

FIG. 6: Representative traces showing changes in (A) total lung volume ($V_T$, ml), and (B) airflow (ml/sec). The vertical lines indicate the point mid-expiration at which $EF_{50}$ is determined.

Figure 7:
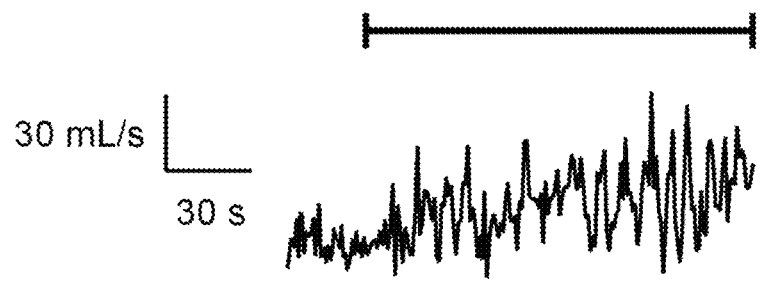
Figure 7:
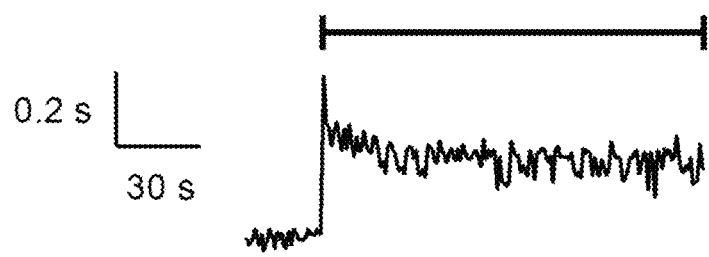

FIG. 7: A: Representative experimental record illustrating change in mid-expiratory flow (EF50) in response to electrical stimulation of the right vagus nerve in a rat. Bar indicates application of 60 μA electrical stimulation with 0.01 ms pulse width at a frequency of 100 Hz.; B: Representative experimental record illustrating change in expiratory time ($T_E$) in response to electrical stimulation of the right vagus nerve in a rat. Bar indicates application of 60 μA electrical stimulation with 0.01 ms pulse width at a frequency of 100 Hz.

Figure 8:
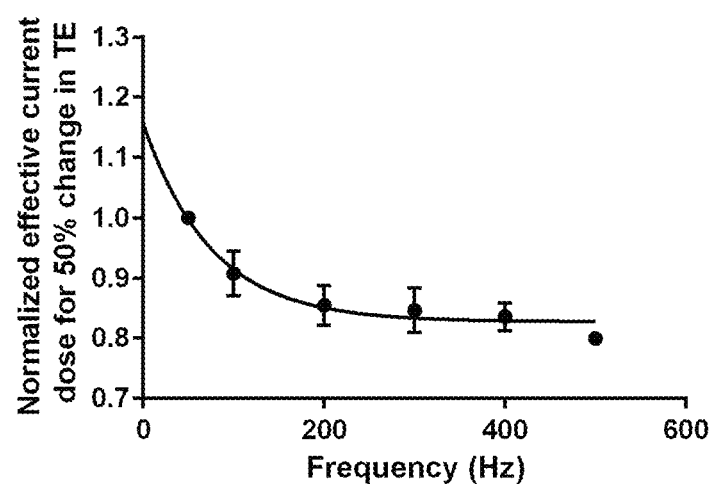

FIG. 8: Group data showing effect of stimulation frequency on the current dose eliciting a 50% change in $T_E$ in rats. Stimulation was on the right cervical vagus nerve (0.01 ms pulse width, current amplitude 80-480 μA). Data are mean±SEM, n=3.

Figure 9:
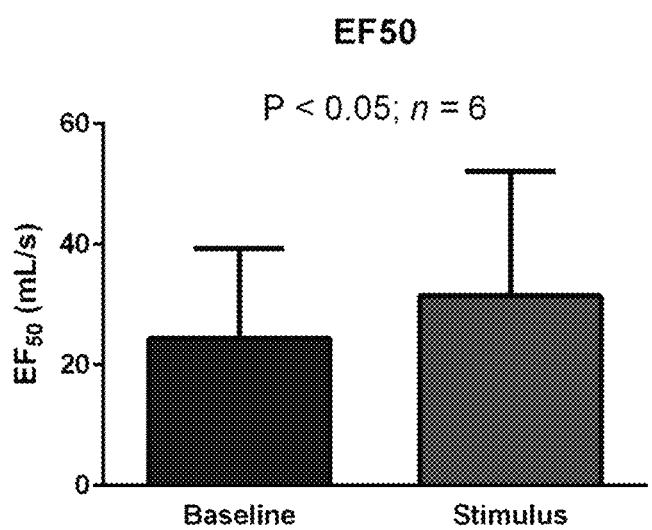
Figure 9:
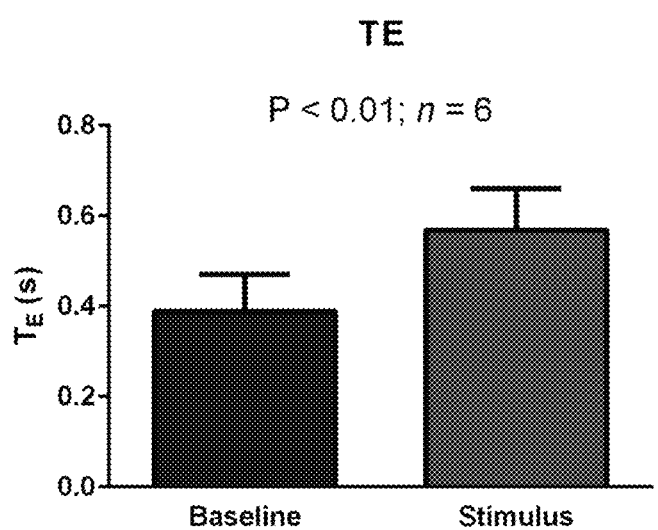

FIG. 9: A: Group data showing electrical stimulation of right vagus nerve increases mid-expiratory flow (EF50) compared to baseline; B: Group data showing electrical stimulation of right vagus nerve increases expiratory time ($T_E$) compared to baseline. Data are mean±SD. Statistical comparisons were made using paired t-test. *, $P<0.05$; n=6).

Figure 10:
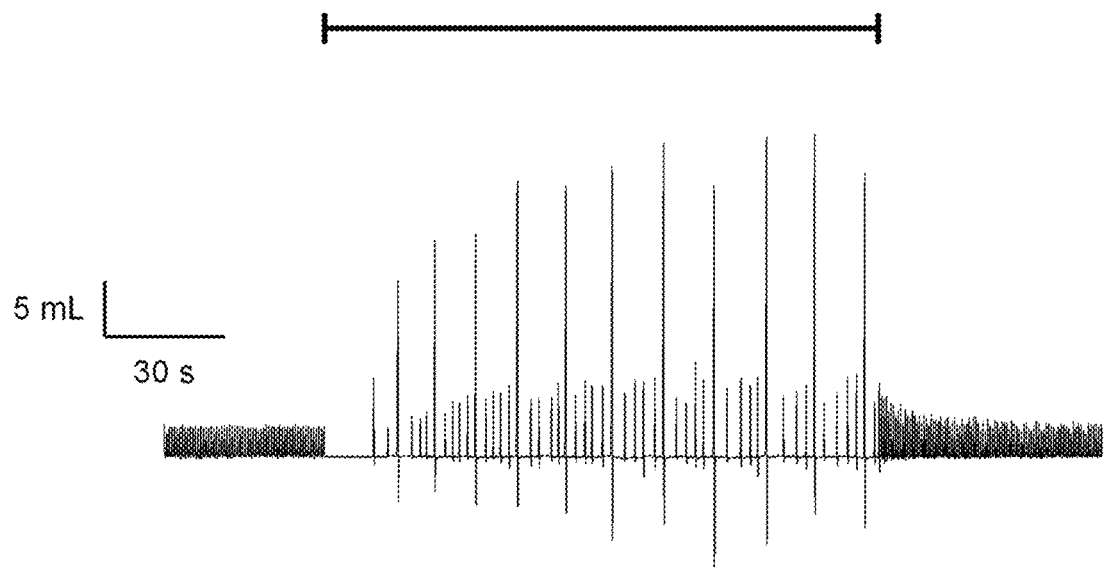

FIG. 10: Experimental record illustrating effect of higher stimulation intensity on tidal volume. Note that 11 augmented breaths (sighs) were elicited. The recording was made in the same rat as in FIG. 7. Bar indicates application of 90 μA electrical stimulation with 0.01 ms pulse width at a frequency of 100 Hz.

Figure 11:
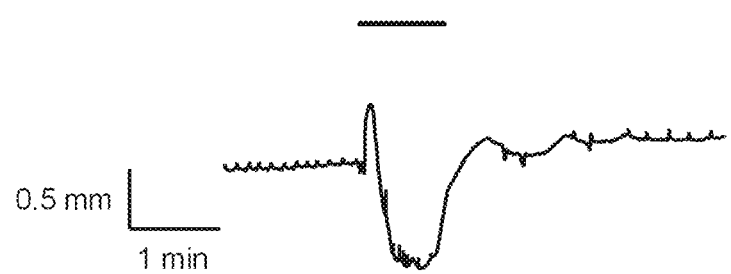
Figure 11:
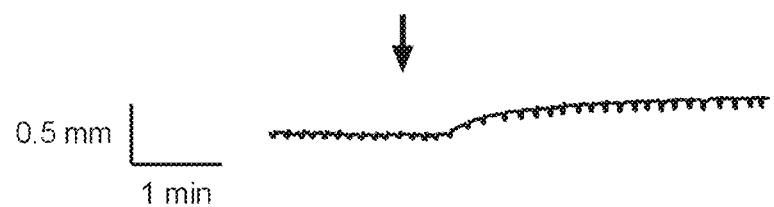

FIG. 11: Stimulation of the cervical vagus using short pulse width electrical pulses causes relaxation of the trachea comparable to that of atropine. A: Representative trace in an acute dog (24.8 kg) preparation illustrating effect of bilateral vagal stimulation on airway dimensions, measured using sonomicrometry crystals implanted into the extrathoracic trachealis muscle. Note the initial transient upward deflection indicating increased distance between the crystal pair, suggesting relaxation of the trachealis. Bar indicates duration of electrical stimulation (0.01 ms pulse width, 20 Hz, 8 mA). B: Representative trace in the same dog preparation illustrating the effect of atropine on relaxation of the trachealis muscle. Arrow indicates saline flush of catheter prefilled with atropine (300 μg/kg i.v.)

The terms as used herein are given their conventional definition in the art as understood by the skilled person, unless otherwise defined below. In the case of any inconsistency or doubt, the definition as provided herein should take precedence.

As used herein, application of a signal may equate to the transfer of energy in a suitable form to carry out the intended effect of the signal. That is, application of a signal to a nerve or nerves may equate to the transfer of energy to (or from) the nerve(s) to carry out the intended effect. For example, the energy transferred may be electrical, mechanical (including acoustic, such as ultrasound), electromagnetic (e.g. optical), magnetic or thermal energy. It is noted that application of a signal as used herein does not include a pharmaceutical intervention.

As used herein, "transducer" is taken to mean any element of applying a signal to the nerve or plexus, for example an electrode, diode, Peltier element or ultrasound transducer.

As used herein, a "non-destructive signal" is a signal as defined above that, when applied, does not irreversibly damage the underlying neural signal conduction ability. That is, application of a non-destructive signal maintains the ability of the nerve or nerves (or fibres thereof) to conduct action potentials when application of the signal ceases, even if that conduction is in practice inhibited or blocked as a result of application of the non-destructive signal. Ablation and cauterisation of at least part of the nerve are examples of destructive signals.

As used herein, "neural activity" of a nerve is taken to mean the signalling activity of the nerve, for example the amplitude, frequency and/or pattern of action potentials in the nerve.

Modulation of neural activity, as used herein, is taken to mean that the signalling activity of the nerve is altered from the baseline neural activity—that is, the signalling activity of the nerve in the patient prior to any intervention. Such modulation may increase, inhibit (for example block), or otherwise change the neural activity compared to baseline activity.

Where the modulation of neural activity is stimulation of neural activity, this may be an increase in the total signalling activity of the whole nerve, or that the total signalling activity of a subset of nerve fibres of the nerve is increased, compared to baseline neural activity in that part of the nerve. For the avoidance of doubt, stimulation of neural activity as used herein is taken to mean a functional stimulation resulting in a functional increase in signalling activity. That is, the increase in signalling activity in the stimulated nerve is able to be effectively transmitted to synaptically-connected cells (e.g. nerves), resulting in a corresponding increase in activity in the synaptically-connected cells. Stimulation of neural activity as used herein is not intended to encompass modulation of neural activity that is intended to inhibit (e.g. block) effective synaptic signalling, even when the inhibitory modulation is a result of an increase in action potential frequency to super-normal levels.

It is thus noted that, in the language of this specification, US2015/0202437 does not describe stimulation of a vagal nerve resulting in bronchodilation.

Modulation of neural activity may also be an alteration in the pattern of action potentials. It will be appreciated that the pattern of action potentials can be modulated without necessarily changing the overall frequency or amplitude. For example, modulation of the neural activity may be such that the pattern of action potentials is altered to more closely resemble a healthy state rather than a disease state.

Modulation of neural activity may comprise altering the neural activity in various other ways, for example increasing or inhibiting a particular part of the neural activity and/or stimulating new elements of activity, for example in particular intervals of time, in particular frequency bands, according to particular patterns and so forth. Such altering of neural activity may for example represent both increases and/or decreases with respect to the baseline activity.

Modulation of neural activity may be selective for certain nerve fibres. As used herein, "selective modulation", for example "selective stimulation", is used to mean that the signal preferentially increases the neural activity in a target class of nerve fibre compared to other classes of nerve fibre. Such a selective modulation is characterised by an increase in the proportion of the target nerve fibres that show modulation of neural activity compared to the proportion of nerve fibres of other classes that show modulation of neural activity. For example, selective stimulation of afferent nerve fibres compared to efferent nerve fibres would result in increased neural activity in a greater proportion of afferent nerve fibres than efferent nerve fibres. Substantially selective stimulation is characterised by neural activity being increased in at least 70% of the target nerve fibres when neural activity is increased in no more than 10% of non-target nerve fibres.

Modulation of the neural activity may be temporary. As used herein, "temporary" is taken to mean that the modulated neural activity (whether that is an increase, inhibition, block or other modulation of neural activity or change in pattern versus baseline activity) is not permanent. That is, the neural activity following cessation of the signal is substantially the same as the neural activity prior to the signal being applied—i.e. prior to modulation.

Modulation of the neural activity may be persistent. As used herein, "persistent" is taken to mean that the modulated neural activity (whether that is an increase, inhibition, block or other modulation of neural activity or change in pattern versus baseline activity) has a prolonged effect. That is, upon cessation of the signal, neural activity in the nerve remains substantially the same as when the signal was being applied—i.e. the neural activity during and following modulation is substantially the same.

Modulation of the neural activity may be corrective. As used herein, "corrective" is taken to mean that the modulated neural activity (whether that is an increase, inhibition, block or other modulation of neural activity or change in pattern versus baseline activity) alters the neural activity towards the pattern of neural activity in a healthy individual. That is, upon cessation of the signal, neural activity in the nerve more closely resembles the pattern of action potentials in the nerve observed in a healthy subject than prior to modulation, preferably substantially fully resembles the pattern of action potentials in the nerve observed in a healthy subject.

Such corrective modulation caused by the signal can be any modulation as defined herein. For example, application of the signal may result in a block on neural activity, and upon cessation of the signal, the pattern of action potentials in the nerve resembles the pattern of action potentials observed in a healthy subject. By way of further example, application of the signal may result in modulation such that the neural activity resembles the pattern of action potentials observed in a healthy subject, and upon cessation of the signal, the pattern of action potentials in the nerve resembles the pattern of action potentials observed in a healthy individual.

As used herein, "a vagal nerve" is taken to refer to a nerve or nerve fibres ultimately derived from the tenth cranial nerve (CN X) and branches thereof. A vagal nerve may be a vagal nerve branch, for example a cervical vagal nerve or a pulmonary vagal nerve. As the skilled person is aware, the vagus nerve has left and right components. Therefore, "a vagal nerve" can refer to either the left or right vagal nerve, unless specified.

As used herein, "A fibres", "Aδ fibres" and "C fibres" of the vagal nerve are taken to refer to those classes of fibres carrying each of the three waves of a compound action potential, as defined in Carr M J and Undem B J, Respirology (2003); 8, 291-301, which is incorporated herein by reference in its entirety, and in particular in reference to the definition of A fibres (also referred to as Aβ fibres), Aδ fibres, and C fibres. A fibres are those which carry the first wave of a compound action potential, Aδ fibres are those which carry the second wave of a compound action potential, C fibres are those which carry the third wave of a compound action potential (FIG. 1). Relative conduction velocity of a compound action potential in a complex mixed nerve decreases from A fibres, to Aδ fibres, to C fibres. Typically, C fibres are thin unmyelinated fibres, Aδ fibres are thin myelinated fibres, and A fibres are thicker myelinated fibres As used herein, bronchoconstriction and bronchospasm are used interchangeably to mean aberrant contraction of the airway smooth muscle (ASM). The skilled person will appreciate that in a healthy individual there is an ongoing background level of ASM contraction. Aberrant contraction of the ASM is a level of contraction that exceeds this background level. Bronchoconstriction may be acute or chronic, transient or permanent. An aberrant contraction of the airway smooth muscle (ASM) may be characterised by, for example, shortness of breath or wheezing. Causes of aberrant contractions of the airway smooth muscle (ASM) include (but are not limited to) pulmonary inflammation, pulmonary infection, stress, sensory irritation and allergens. Bronchoconstriction is one of the symptoms of both chronic obstructive pulmonary disease (COPD) and asthma.

As used herein, the neural activity in the vagus nerve of a healthy individual is that neural activity exhibited by a patient not undergoing bronchoconstriction.

As used herein, an "improvement in a measurable physiological parameter" is taken to mean that for any given physiological parameter, an improvement is a change in the value of that parameter in the patient towards the normal value or normal range for that value—i.e. towards the expected value in a healthy individual.

For an example, in a patient suffering from bronchoconstriction, an improvement in a measurable parameter may be: a reduction in parasympathetic tone, a decrease in airway smooth muscle tone, an increase in blood oxygen saturation, a decrease in blood carbon dioxide concentration, an increase in tidal mid-expiratory flow, a decrease in respiratory rate, an increase in total lung capacity, an increase in forced expiration volume.

The physiological parameter may comprise an action potential or pattern of action potentials in a nerve of the patient. An improvement in such a parameter is characterised by the action potential or pattern of action potentials in the nerve more closely resembling that exhibited by a healthy individual than before the intervention.

As used herein, a physiological parameter is not affected by modulation of the neural activity if the parameter does not change as a result of the modulation from the average value of that parameter exhibited by the subject or patient when no intervention has been performed—i.e. it does not depart from the baseline value for that parameter.

The skilled person will appreciate that the baseline for any neural activity or physiological parameter in an individual need not be a fixed or specific value, but rather can fluctuate within a normal range or may be an average value with associated error and confidence intervals. Suitable methods for determining baseline values would be well known to the skilled person.

As used herein, a measurable physiological parameter is detected in a patient when the value for that parameter exhibited by the patient at the time of detection is determined. A detector is any element able to make such a determination.

As used herein, a patient is refractory to bronchodilator treatment if bronchodilator treatment (e.g. anticholinergic or beta-adrenoreceptor agonist treatment) does not effectively manage the patient's bronchoconstriction symptoms. Such a refractory nature may be acute (for example during a severe asthma attack) or chronic (for example, a long term non-responder).

A "predefined threshold value" for a physiological parameter is the value for that parameter where that value or beyond must be exhibited by a subject or patient before the intervention is applied. For any given parameter, the threshold value may be a value indicative of imminent or ongoing bronchospasm. Examples of such predefined threshold values include parasympathetic tone (neural, hemodynamic (e.g. heart rate, blood pressure, heart rate variability) or circulating plasma/urine biomarkers) greater than a threshold parasympathetic tone, or greater than parasympathetic tone in a healthy individual; ASM tone greater than a threshold ASM tone, or greater than ASM tone in a healthy individual; blood oxygen saturation lower than that characteristic of a healthy individual; blood carbon dioxide concentration greater than that characteristic of a healthy individual; a mid-expiratory flow lower than that characteristic of a healthy individual; a total lung capacity lower than that characteristic of a healthy individual; a forced expiration volume lower than that characteristic of a healthy individual. Appropriate values for any given parameter would be simply determined by the skilled person.

Such a threshold value for a given physiological parameter is exceeded if the value exhibited by the patient is beyond the threshold value—that is, the exhibited value is a greater departure from the normal or healthy value for that parameter than the predefined threshold value.

Treatment of bronchoconstriction as used herein may be prophylactic or therapeutic. Prophylactic treatment may be characterised by the patient exhibiting less frequent or less severe episodes of bronchoconstriction than before treatment. Therapeutic treatment may be characterised by amelioration of an ongoing bronchospasm. For example, therapeutic treatment is applied when the patient is experiencing bronchoconstriction and results in at least partial relief of the bronchoconstriction, preferably full relief of the bronchoconstriction (i.e. a return to healthy phenotype). Treatment of COPD and treatment of asthma as used herein is characterised at least by treatment of bronchoconstriction associated with said conditions.

A "neuromodulation device" or "neuromodulation apparatus" as used herein is a device configured to modulate the neural activity of a nerve. "Device" and "apparatus" are used interchangeably herein. Neuromodulation devices as described herein comprise at least one transducer capable of effectively applying a signal to a nerve. In those embodiments in which the neuromodulation device is at least partially implanted in the patient, the elements of the device that are to be implanted in the patient are constructed such that they are suitable for such implantation. Such suitable constructions would be well known to the skilled person. Indeed, various fully implantable neuromodulation devices are currently available, such as the vagus nerve stimulator of SetPoint Medical, in clinical development for the treatment of rheumatoid arthritis (*Arthritis & Rheumatism*, Volume 64, No. 10 (Supplement), page S195 (Abstract No. 451), October 2012. *"Pilot Study of Stimulation of the Cholinergic Anti-Inflammatory Pathway with an Implantable Vagus Nerve Stimulation Device in Patients with Rheumatoid Arthritis"*, Frieda A. Koopman et al), and the INTERSTIM™ device (Medtronic, Inc), a fully implantable device utilised for sacral nerve modulation in the treatment of overactive bladder.

As used herein, "implanted" is taken to mean positioned at least partially within the patient's body. Partial implantation means that only part of the device is implanted—i.e. only part of the device is positioned within the patient's body, with other elements of the device external to the patient's body. Wholly implanted means that the entire of the device is positioned within the patient's body. For the avoidance of doubt, the device being "wholly implanted" does not preclude additional elements, independent of the device but in practice useful for its functioning (for example, a remote wireless charging unit or a remote wireless manual override unit), being independently formed and external to the patient's body.

As shown herein, it has been identified that bronchoconstriction, such as COPD-associated and asthma-associated bronchoconstriction, can be relieved and/or prevented by stimulation of neural activity in a vagus nerve—that is, a nerve or nerve fibres ultimately derived from the tenth cranial nerve (CN X) and branches thereof. It is further demonstrated herein that different vagal nerve fibre classes can be selectively stimulated based on the current of the electrical signal for any given pulse duration. Afferent nerve fibres may be selectively stimulated in preference to efferent nerve fibres as afferent fibres have a lower stimulatory threshold. Similarly, of the afferent fibres, A fibres may be selectively stimulated in preference to Aδ fibres and C fibres, as A fibres have a lower stimulatory threshold than Aδ and C fibres (see Examples and FIG. 3). It will be appreciated that the precise signal parameters (for example, current/voltage) required to achieve the intended selective stimulation of afferent vagal fibres or of vagal A fibres will vary from patient to patient due to inherent variation in nerve size and relative positioning of the transducer(s). However, in light of the information presented herein, the skilled person would be able to select the appropriate signal parameters (e.g. current/voltage) to achieve the intended selective stimulation. For example, the skilled person is aware of methods suitable to monitor the neural activity profile induced by nerve stimulation. By further example, parameters that achieve selective afferent fibre stimulation will be indicated by bronchodilation being exhibited by the subject, for example by an increase in their EF50 and/or an increase in expiration time. Selective stimulation of afferent A fibres in preference to Aδ fibres can be further indicated by more effective bronchodilation, and/or an absence of RAR activity-associated augmented breaths.

It is further demonstrated herein that the differentiation of afferent A fibres from Aδ and C nerve fibres for the purposes of selective stimulation is enhanced at low pulse durations. In particular, the absolute difference (which is observed at all pulse durations) between the stimulation threshold for A fibres and the stimulation threshold for Aδ nerve fibres is widened at pulse durations less than or equal to 0.06 ms (see FIG. 3). The widening of the distance between the stimulation threshold of A fibres compared to that of Aδ fibres is more pronounced the lower the pulse duration, with the widest gap observed at 0.01 ms (FIG. 3). When fitting a neuromodulatory device to a patient, this widened gap between stimulation thresholds allows easier tuning of the signal parameters to obtain the desired selective stimulation. For example, at lower pulse durations, the resolution of the current able to be accurately applied by the device does not need to be as high in order to achieve differential and selective stimulation.

Surprisingly, it is particularly advantageous to stimulate neural activity in afferent fibres of the vagal nerve to treat said bronchoconstriction. Doing so limits the possibility of unwanted side-effects on other bodily systems controlled by the vagus nerve. It is further identified herein that it is more advantageous to selectively stimulate the afferent A fibres of the vagal nerve in preference to Aδ and C fibres because this selective stimulation avoids cross-stimulation of RAR-associated signalling. By targeting afferent A fibres, it is therefore intended to further limit side-effects and cross-reactivity associated with the neuromodulation as well as to achieve a more effective treatment of bronchoconstriction.

A neuromodulation device that stimulates neural activity in a vagal nerve will therefore provide an effective treatment for bronchoconstriction, for example COPD- or asthma-associated bronchoconstriction.

Such a device can be advantageously used in conjunction with a bronchodilator, for example an anticholinergic (e.g. atropine, amfebutamone) or β2-receptor agonists (e.g. salbutamol). For example, devices and methods in accordance with the invention can be used by patients chronically taking a bronchodilator to treat ongoing asthma or COPD. By using the device or method of the invention, it is expected that the amount and/or frequency of administration of bronchodilator can be reduced, thereby improving patient compliance.

Devices and methods according to the invention may also be used advantageously by patients that are refractory to or unable to have a bronchodilator administered. An example of such a group of patients is difficult or brittle asthma patients. Such a patient undergoing a severe attack of asthma is frequently inadequately responsive to inhaled bronchodilators. Devices and methods according to the invention can be used in such refractory patients to supplement, augment or replace pharmaceutical therapy.

Therefore, in accordance with a first aspect of the invention there is provided an apparatus for stimulating neural activity in a vagal nerve of a patient, the apparatus comprising one or more transducers each configured to apply a signal to said vagal nerve of the patient, and a controller coupled to the one or more transducers, the controller controlling the signal to be applied by each of the one or more transducers, such that the signal stimulates the neural activity of said nerve to produce a physiological response in the patient.

In certain embodiments, the signal applied by the one or more transducers is a non-destructive signal.

In certain such embodiments, the signal applied by the one or more transducers is an electrical signal, an optical signal, an ultrasonic signal, or a thermal signal. In those embodiments in which the apparatus has at least two transducers, the signal which each of the transducers is configured to apply is independently selected from an electrical signal, an optical signal, an ultrasonic signal, and a thermal signal. That is, each transducer may be configured to apply a different signal. Alternatively, in certain embodiments each transducer is configured to apply the same signal.

In certain embodiments, each of the one or more transducers may be comprised of one or more electrodes, one or more photon sources, one or more ultrasound transducers, one more sources of heat, or one or more other types of transducer arranged to put the signal into effect.

In certain embodiments, the signal or signals applied by the one or more transducers is an electrical signal, for example a voltage or current. In such embodiments, the one or more transducers configured to apply the electrical signal are electrodes, for example wire electrodes or cuff electrodes. In certain such embodiments the signal applied comprises a direct current (DC) waveform, such as a charge balanced direct current waveform, or an alternating current (AC) waveform, or both a DC and an AC waveform. In certain embodiments, the signal comprises a DC waveform of sub-kilohertz frequency.

In certain embodiments, the DC waveform or AC waveform may be a square, sinusoidal, triangular or complex waveform. The DC waveform may alternatively be a constant amplitude waveform. In certain embodiments the electrical signal is a DC square waveform of varying voltage.

In certain embodiments wherein the signal is an electrical signal, the electrical signal has a pulse duration of 0.005-0.1 ms, optionally 0.01-0.06 ms. optionally 0.01-0.05 ms, optionally 0.01-0.04 ms. In certain preferred embodiments the signal has a pulse duration of 0.01-0.03 ms, more preferably 0.01-0.02 ms.

In certain embodiments wherein the signal is an electrical signal the signal has a pulse duration of less than or equal to 0.1 ms, optionally less than or equal to 0.06 ms, optionally less than or equal to 0.05 ms, optionally less than or equal to 0.04 ms, optionally less than or equal to 0.03 ms, optionally less than or equal to 0.02 ms, optionally less than or equal to 0.01 ms. In certain preferred embodiments the signal has a pulse duration of 0.01 ms or 0.02 ms or 0.04 ms.

In certain embodiments, the signal comprises a DC square waveform of 100 Hz, pulse duration 0.01 ms, or a DC square waveform of 100 Hz, pulse duration 0.02 ms. In certain other embodiments, the signal comprises a DC square waveform of at least 200 Hz, pulse duration 0.01 ms. In certain embodiments, the signal comprises a DC square waveform of 50-500 Hz, pulse duration 0.01 ms. In certain embodiments, the signal comprises a DC square waveform of between 20 and 200 Hz, pulse duration 0.01 ms.

In certain preferred embodiments, wherein the signal comprises one or more DC waveforms, each DC waveform is independently selected from a DC waveform having a frequency in the range of 1 Hz-1 kHz, optionally 1-500 Hz, optionally 1-200 Hz. In certain preferred embodiments the signal comprises a DC waveform having a frequency of 50-150 Hz. In certain preferred embodiments the signal comprises a DC waveform having a frequency of 100 Hz.

It will be appreciated by the skilled person that the current amplitude of an applied electrical signal necessary to achieve the intended stimulation will depend upon the positioning of the electrode and the associated electrophysiological characteristics (e.g. impedance). It is within the ability of the skilled person to determine the appropriate current amplitude for achieving the intended stimulation in a given subject. For example, the skilled person is aware of methods suitable to monitor the neural activity profile induced by nerve stimulation.

In certain embodiments, the electrical signal comprises a DC waveform and/or an AC waveform having a current of 1-8000 µA, 1-7000 µA, 1-6000 µA, 1-5000 µA, 1-4000 µA, 10-4000 µA, 10-3000 µA, 10-2000 µA, optionally 20-1000 µA, optionally 20-500 µA, optionally 50-250 µA. In certain embodiments the electrical signal has a current of at least at least 10 μA, 20 μA, at least 50 μA, at least 60 μA, at least 70 μA, at least 80 μA, at least 90 μA, at least 100 μA, at least 110 μA, at least 150 μA, at least 180 μA, at least 200 μA, at least 220 μA, at least 250 μA, at least 300 μA, at least 400 μA, at least 500 μA, at least 600 μA, at least 700 μA, at least 800 μA, at least 900 μA, at least 1000 μA, at least 1200 μA, at least 1500 μA, at least 2000 μA, at least 3000 μA, at least 4000 μA, at least 5000 μA, at least 6000 μA, at least 7000 μA, at least 8000 μA. In certain embodiments, the electrical signal comprises a DC waveform and/or an AC waveform having a current of between 80 and 480 μA. In certain alternative embodiments, the electrical signal comprises a DC waveform and/or an AC waveform having a current of 8 mA.

In certain such embodiments, all the transducers are electrodes configured to apply an electrical signal, optionally the same electrical signal.

In certain embodiments wherein the signal applied by the one or more transducers is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In those embodiments in which the signal applied by the one or more transducers is a thermal signal, at least one of the one or more transducers is a transducer configured to apply a thermal signal. In certain such embodiments, all the transducers are configured to apply a thermal signal, optionally the same thermal signal.

In certain embodiments, one or more of the one or more transducers comprise a Peltier element configured to apply a thermal signal, optionally all of the one or more transducers comprise a Peltier element. In certain embodiments, one or more of the one or more transducers comprise a laser diode configured to apply a thermal signal, optionally all of the one or more transducers comprise a laser diode configured to apply a thermal signal. In certain embodiments, one or more of the one or more transducers comprise a electrically resistive element configured to apply a thermal signal, optionally all of the one or more transducers comprise a electrically resistive element configured to apply a thermal signal.

In certain embodiments the signal applied by the one or more transducers is a mechanical signal, optionally an ultrasonic signal. In certain alternative embodiments, the mechanical signal applied by the one or more transducers is a pressure signal.

In certain embodiments the signal applied by the one or more transducers is an electromagnetic signal, optionally an optical signal. In certain such embodiments, the one or more transducers comprise a laser and/or a light emitting diode configured to apply the optical signal.

In certain embodiments, the physiological response produced in the patient is one or more of: relief or prevention of bronchoconstriction, a reduction in parasympathetic tone, an increase in sympathetic tone, a decrease in airway smooth muscle (ASM) tone, an increase in blood oxygen saturation, a decrease in blood carbon dioxide concentration, a decrease in respiratory rate, an increase in total lung capacity, an increase in mid-expiratory flow, an increase in expiration time, an increase in forced expiration volume, and the pattern of action potentials in the vagus nerve more closely resembling that exhibited by a healthy individual than before the intervention.

In certain embodiments, the apparatus further comprises a detector element to detect one or more physiological parameters in the patient. Such a detector element may be configured to detect the one or more physiological parameters. That is, in such embodiments each detector may detect more than one physiological parameter, for example two, three, four or all the detected physiological parameters. Alternatively, in such embodiments each of the one or more detector elements is configured to detect a separate parameter of the one or more physiological parameters detected.

In such certain embodiments, the controller is coupled to the detector element configured to detect one or more physiological parameters, and causes the transducer or transducers to apply the signal when the physiological parameter is detected to be meeting or exceeding a predefined threshold value.

In certain embodiments, the one or more detected physiological parameters are selected from: parasympathetic tone, sympathetic tone, ASM tone, blood oxygen saturation, blood carbon dioxide concentration, mid-expiratory flow, expiration time, respiratory rate, total lung capacity, and forced expiration volume.

In certain embodiments, the one or more detected physiological parameters comprise an action potential or pattern of action potentials in a nerve of the patient, wherein the action potential or pattern of action potentials is associated with bronchoconstriction. In certain such embodiments, the nerve is a vagal nerve. In certain such embodiments, the nerve is a cervical vagal nerve or a pulmonary branch of the vagal nerve. In certain embodiments, the action potential or pattern of action potentials is detected in efferent fibres of a vagal nerve, preferably efferent fibres of a cervical vagal nerve or a pulmonary branch of the vagal nerve. Alternatively, in certain embodiments, the action potential or pattern of action potentials is detected in afferent fibres of a vagal nerve, preferably afferent fibres of a cervical vagal nerve or a pulmonary branch of the vagal nerve.

It will be appreciated that any two or more of the indicated physiological parameters may be detected in parallel or consecutively. For example, in certain embodiments, the controller is coupled to a detector or detectors configured to detect the pattern of action potentials in a cervical vagal nerve and also the blood oxygen saturation of the patient.

The inventors have identified that bronchoconstriction can be relieved and/or prevented by stimulating neural activity in a vagus nerve—that is, by stimulating neural activity in a nerve ultimately derived from the tenth cranial nerve (CN X) and branches thereof. In certain embodiments, the nerve to which the signal is applied is a cervical vagal nerve or, alternatively, a pulmonary vagal nerve.

Surprisingly, it is particularly advantageous to stimulate neural activity of afferent fibres of the vagal nerve to treat bronchoconstriction, for example bronchoconstriction associated with COPD or asthma. It is further advantageous to selectively stimulate neural activity of afferent A fibres of the vagal nerve to treat bronchoconstriction.

Such stimulation of the vagal nerve, in particular selective stimulation of the afferent fibres, and further selectively, the A fibres will limit the possibility of unwanted side-effects on other bodily systems controlled by the vagus nerve. By targeting these nerves fibres, it is therefore intended to further limit side-effects and cross-reactivity associated with the neuromodulation.

Stimulation of neural activity as a result of applying the signal is an increase in neural activity in the nerve or nerves to which the signal is applied. That is, in such embodiments, application of the signal results in the neural activity in at least part of the nerve or nerves to which the signal is applied (for example specific classes of nerve fibre in the nerve or nerves) being increased compared to the baseline neural activity in that part of the nerve. Such stimulation of neural activity could equally be across the whole nerve, in which case neural activity would be increased across the whole nerve or nerves. For the avoidance of doubt, stimulation of neural activity as used herein is taken to mean a functional increase in signalling activity in the indicated nerve or nerve fibres.

Therefore, in certain embodiments, the signal stimulates, preferably selectively stimulates, neural activity in afferent fibres of the vagal nerve. In certain preferred embodiments, the signal stimulates neural activity, preferably selectively stimulates neural activity, in afferent A fibres of the vagal nerve. In certain preferred embodiments the signal substantially selectively stimulates neural activity in afferent fibres of the vagal nerve. In certain preferred embodiments the signal substantially selectively stimulates neural activity in afferent A fibres of the vagal nerve.

In certain embodiments, the signal is applied to the specified nerve on the left-side of the patient, the specified nerve on the right-side of the patient, or both. That is, in certain embodiments the signal is applied unilaterally or, alternatively, bilaterally.

In certain embodiments, application of the signal to a nerve or nerve results in the modulation in neural activity that is an alteration to the pattern of action potentials in all or part of the nerve or nerves. In certain such embodiments, the neural activity is modulated such that the resultant pattern of action potentials in the nerve or nerves resembles the pattern of action potentials in the nerve or nerves observed in a healthy subject.

Modulation of neural activity may comprise altering the neural activity in various other ways, for example increasing or inhibiting a particular part of the activity and stimulating new elements of activity, for example in particular intervals of time, in particular frequency bands, according to particular patterns and so forth. Such altering of neural activity may for example represent both increases and/or decreases with respect to the baseline activity.

In certain embodiments, the controller causes the signal to be applied intermittently. In certain such embodiments, the controller causes the signal to applied for a first time period, then stopped for a second time period, then reapplied for a third time period, then stopped for a fourth time period. In such an embodiment, the first, second, third and fourth periods run sequentially and consecutively.

The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments wherein the controller causes the signal to be applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the controller causes the signal to be applied intermittently, the signal is applied only when the patient is in a specific physiological state. In certain such embodiments, the signal is applied only when the patient is in a state of bronchospasm.

In certain such embodiments, the apparatus further comprises a communication, or input, element via which the status of the patient (e.g. that they are experiencing bronchospasm) can be indicated by the patient or a physician. In alternative embodiments, the apparatus further comprises a detector configured to detect the status of the patient, wherein the signal is applied only when the detector detects that the patient is in the specific state.

In certain alternative embodiments, the controller causes the signal to be permanently applied. That is, once begun, the signal is continuously applied to the nerve or nerves. It will be appreciated that in embodiments wherein the signal is a series of pulses, gaps between pulses do not mean the signal is not continuously applied.

In certain embodiments of the apparatus, the modulation in neural activity caused by the application of the signal is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments, the modulation in neural activity caused by the application of the signal or signals is substantially persistent. That is, upon cessation of the signal, neural activity in the nerve or nerves remains substantially the same as when the signal was being applied—i.e. the neural activity during and following modulation is substantially the same.

In certain embodiments, the modulation in neural activity caused by the application of the signal is partially corrective, preferably substantially corrective. That is, upon cessation of the signal, neural activity in the nerve or nerves more closely resembles the pattern of action potentials in the nerve(s) observed in a healthy subject than prior to modulation, preferably substantially fully resembles the pattern of action potentials in the nerve(s) observed in a healthy subject. In such embodiments, the modulation caused by the signal can be any modulation as defined herein. For example, application of the signal may result in stimulation of neural activity, and upon cessation of the signal, the pattern of action potentials in the nerve or nerves resembles the pattern of action potentials observed in a healthy individual. It is hypothesised that such a corrective effect is the result of a positive feedback loop—that is, the underlying cause of or predisposition to bronchoconstriction, for example as a result of asthma or COPD, is treated as result of the device and the claimed methods.

In certain embodiments, the apparatus is suitable for at least partial implantation into the patient. In certain such embodiments, the apparatus is suitable to be wholly implanted in the patient.

In certain embodiments, the apparatus further comprises one or more power supply elements, for example a battery, and/or one or more communication elements.

In certain embodiments, the patient is refractory to bronchodilator treatment. That is, bronchodilator treatment is not in itself sufficient to fully treat bronchoconstriction in the patient. Therefore, stimulation of neural activity in a vagal nerve of the patient by a device according to the invention provides an additional therapeutic option that may be used as an adjunct to or alternative to bronchodilator therapy. In certain embodiments, the patient is a patient suffering from "difficult asthma" or brittle asthma. Such patients are refractory to bronchodilator therapy, for example when undergoing a severe asthma attack. A device according to the invention is therefore expected to be particularly advantageous in such patients, providing an adjunct to or alternative to bronchodilator therapy.

In a second aspect, the invention provides a method for treating bronchoconstriction in a patient, in particular bronchoconstriction associated with COPD or asthma, the method comprising implanting an apparatus according to the first aspect, positioning at least one transducer of the apparatus in signalling contact with a vagal nerve of the patient, and activating the apparatus. In such embodiments, the transducer is in signalling contact with the nerve when it is positioned such that the signal can be effectively applied to the nerve. The apparatus is activated when the apparatus is in an operating state such that the signal will be applied as determined by the controller.

In certain such embodiments, a first transducer is positioned in signalling contact with a left vagal nerve of said patient to stimulate neural activity in said left nerve in the patient, and a second transducer is positioned in signalling contact with a right vagal nerve of said patient to stimulate neural activity in said right nerve in the patient. In certain such embodiments, the first and second transducers are part of one apparatus according to the first aspect. In alternative such embodiments, the first and second transducers are part of separate apparatuses according to the first aspect.

In certain embodiments, the vagal nerve or nerves is a cervical vagal nerve or a pulmonary branch of the vagal nerve. In certain embodiments, the apparatus is in signalling contact with the afferent fibres of the vagal nerve, optionally the afferent A fibres of the vagal nerve.

In certain embodiments, the method further comprises administration of a bronchodilator to the patient. In certain such embodiments, the bronchodilator is an anticholinergic compound (for example atropine or amfebutamone) or a beta-adrenoreceptor agonist (for example salbutamol).

In certain embodiments, the patient is refractory to bronchodilator treatment. That is, bronchodilator treatment is not in itself sufficient to fully treat bronchoconstriction in the patient. Therefore, stimulation of neural activity in a vagal nerve of the patient according to the invention provides an additional therapeutic option that may be used as an adjunct to or alternative to bronchodilator therapy. In certain such embodiments, the method of the invention further comprises administration of a bronchodilator to the patient. In certain such embodiments, the bronchodilator is an anticholinergic compound (for example atropine or amfebutamone) or a beta-adrenoreceptor agonist (for example salbutamol). In such embodiments, the method of the invention is expected to be an effective treatment due to a combinatorial effect. In certain embodiments, the patient is a patient suffering from "difficult asthma" or brittle asthma. Such patients are refractory to bronchodilator therapy, for example when undergoing a severe asthma attack. Methods according to the invention are therefore expected to be particularly advantageous in such patients, providing an adjunct to or alternative to bronchodilator therapy.

Implementation of all aspects of the invention (as discussed both above and below) will be further appreciated by reference to FIGS. 2A-2C.

FIGS. 2A-2C show how the invention may be put into effect using one or more neuromodulation devices which are implanted in, located on, or otherwise disposed with respect to a patient in order to carry out any of the various methods described herein. In this way, one or more neuromodulation devices can be used to treat bronchoconstriction in a patient, for example bronchoconstriction associated with COPD or asthma, by stimulating neural activity in at least one vagal nerve, for example a cervical vagal nerve or a pulmonary branch of the vagal nerve, optionally selectively stimulating neural activity in the afferent fibres the vagal nerve, optionally selectively stimulating neural activity in the afferent A fibres of the vagal nerve, optionally substantially selectively stimulating neural activity in the afferent fibres of the vagal nerve, optionally substantially selectively stimulating neural activity in the afferent A fibres of the vagal nerve.

In each of the FIGS. 2B-2C a separate neuromodulation device 100 is provided in respect of each of the left and right vagal nerve, although as discussed herein a device could be provided or used in respect of only one of the left and right vagal nerves. Each such neuromodulation device may be fully or partially implanted in the patient, or otherwise located, so as to provide neuromodulation of the respective nerve or nerves. Each of the left and right neuromodulation devices 100 may operate independently, or may operate in communication with each other.

FIG. 2A also shows schematically components of an implanted neuromodulation device 100, in which the device comprises several elements, components or functions grouped together in a single unit and implanted in the patient. A first such element is a transducer 102 which is shown in proximity to a vagal nerve 90 of the patient. The transducer 102 may be operated by a controller element 104. The device may comprise one or more further elements such as a communication element 106, a detector element 108, a power supply element 110 and so forth.

Each neuromodulation device 100 may carry out the required neuromodulation (i.e. stimulation) independently, or in response to one or more control signals. Such a control signal may be provided by the controller 104 according to an algorithm, in response to output of one or more detector elements 108, and/or in response to communications from one or more external sources received using the communications element. As discussed herein, the detector element(s) could be responsive to a variety of different physiological parameters.

FIG. 2B illustrates some ways in which the apparatus of FIG. 2A may be differently distributed. For example, in FIG. 2B the neuromodulation devices 100 comprise transducers 102 implanted proximally to a vagal nerve 90, but other elements such as a controller 104, a communication element 106 and a power supply 110 are implemented in a separate control unit 130 which may also be implanted in, or carried by the patient. The control unit 130 then controls the transducers in both of the neuromodulation devices via connections 132 which may for example comprise electrical wires and/or optical fibres for delivering signals and/or power to the transducers.

In the arrangement of FIG. 2B one or more detectors 108 are located separately from the control unit, although one or more such detectors could also or instead be located within the control unit 130 and/or in one or both of the neuromodulation devices 100. The detectors may be used to detect one or more physiological parameters of the patient, and the controller element or control unit then causes the transducers to apply the signal in response to the detected parameter(s), for example only when a detected physiological parameter meets or exceeds a predefined threshold value. Physiological parameters which could be detected for such purposes include parasympathetic tone, sympathetic tone, ASM tone, blood oxygen saturation, blood carbon dioxide concentration, mid-expiratory flow, expiration time, respiratory rate, total lung capacity, and forced expiration volume. Similarly, a detected physiological parameter could be an action potential or pattern of action potentials in a nerve of the patient, for example a vagal nerve, optionally a cervical vagal nerve or a pulmonary branch of the vagal nerve, wherein the action potential or pattern of action potentials is associated with bronchospasm.

A variety of other ways in which the various functional elements could be located and grouped into the neuromodulation devices, a control unit 130 and elsewhere are of course possible. For example, one or more sensors of FIG. 2B could be used in the arrangement of FIG. 2A or 2C or other arrangements.

FIG. 2C illustrates some ways in which some functionality of the apparatus of FIG. 2A or 2B is provided not implanted in the patient. For example, in FIG. 2C an external power supply 140 is provided which can provide power to implanted elements of the apparatus in ways familiar to the skilled person, and an external controller 150 provides part or all of the functionality of the controller 104, and/or provides other aspects of control of the apparatus, and/or provides data readout from the apparatus, and/or provides a data input facility 152. The data input facility could be used by a patient or other operator in various ways, for example to input data relating to the respiratory status of the patient (e.g. if they are experiencing bronchospasm, their forced expiration volume).

Each neuromodulation device may be adapted to carry out the neuromodulation required (i.e. stimulation, for example selective stimulation) using one or more physical modes of operation which typically involve applying a signal to a vagal nerve, a cervical vagal nerve or a pulmonary branch of a vagal nerve, or the afferent fibres thereof, such a signal typically involving a transfer of energy to (or from) the nerve(s). As already discussed, such modes may comprise stimulating the nerve or nerves using an electrical signal, an optical signal, an ultrasound or other mechanical signal, a thermal signal, a magnetic or electromagnetic signal, or some other use of energy to carry out the required modulation. Such signals may be non-destructive signals. To this end, the transducer 102 illustrated in FIG. 2A could be comprised of one or more electrodes, one or more photon sources, one or more ultrasound transducers, one more sources of heat, or one or more other types of transducer arranged to put the required neuromodulation (i.e. stimulation of neural activity) into effect. Preferably the device is comprised of one or more electrodes configured to apply an electrical signal, for example a wire electrode or a cuff electrode.

The neural modulation device(s) or apparatus may be arranged to stimulate neural activity in a vagal nerve, a cervical vagal nerve or a pulmonary branch of a vagal nerve, the afferent fibres thereof or A fibres thereof by using the transducer(s) to apply a voltage or current, for example a direct current (DC) waveform, such as a charge balanced direct current, or an AC waveform, or both. For the avoidance of doubt, stimulation of neural activity as used herein is taken to mean a functional increase in signalling activity in the indicated nerve or nerve fibres.

In certain embodiments, the DC waveform or AC waveform may be a square, sinusoidal, triangular or complex waveform. The DC waveform may alternatively be a constant amplitude waveform. In certain embodiments the electrical signal is a DC square waveform of varying voltage.

In certain embodiments, the electrical signal is a DC waveform having a frequency in the range of 1 Hz-1 kHz, optionally 1-500 Hz, optionally 1-200 Hz, optionally 50-150 Hz, optionally 100 Hz.

In certain embodiments wherein the signal is an electrical signal, the electrical signal has a pulse duration of 0.005-0.1 ms, optionally 0.01-0.06 ms. optionally 0.01-0.05 ms, optionally 0.01-0.04 ms. In certain preferred embodiments the signal has a pulse duration of 0.01-0.03 ms, more preferably 0.01-0.02 ms.

In certain embodiments wherein the signal is an electrical signal the signal has a pulse duration of less than or equal to 0.1 ms, optionally less than or equal to 0.06 ms, optionally less than or equal to 0.05 ms, optionally less than or equal to 0.04 ms, optionally less than or equal to 0.03 ms, optionally less than or equal to 0.02 ms, optionally less than or equal to 0.01 ms. In certain preferred embodiments the signal has a pulse duration of 0.01 ms or 0.02 ms or 0.04 ms.

In certain preferred embodiments, the signal comprises a DC square waveform of 100 Hz, pulse duration 0.01 ms, or a DC square waveform of 100 Hz, pulse duration 0.02 ms. In certain other embodiments, the signal comprises a DC square waveform of at least 200 Hz, pulse duration 0.01 ms. In certain embodiments, the signal comprises a DC square waveform of 50-500 Hz, pulse duration 0.01 ms. In certain embodiments, the signal comprises a DC square waveform of between 20 and 200 Hz, pulse duration 0.01 ms.

It will be appreciated by the skilled person that the current amplitude of an applied electrical signal necessary to achieve the intended stimulation will depend upon the positioning of the electrode and the associated electrophysiological characteristics (e.g. impedance). It is within the ability of the skilled person to determine the appropriate current amplitude for achieving the intended stimulation in a given subject. For example, the skilled person is aware of methods suitable to monitor the neural activity profile induced by nerve stimulation. By further example, parameters that achieve selective afferent fibre stimulation will be indicated by bronchodilation being exhibited by the subject, for example by an increase in their EF50, and/or an increase in expiration time, and/or a decrease in respiration rate, and/or an increase in forced expiration volume (FEV), and/or relaxation of the trachealis muscle. Selective stimulation of afferent A fibres in preference to Aδ fibres can be further indicated by more effective bronchodilation, and/or an absence of RAR activity-associated augmented breaths.

Selective stimulation of afferent A fibres in preference to Aδ fibres can be further indicated by more effective bronchodilation, and/or an absence of RAR activity-associated augmented breaths.

In certain embodiments, the electrical signal comprises a DC waveform and/or an AC waveform having a current of 1-8000 µA, 1-7000 µA, 1-6000 µA, 1-5000 µA, 1-4000 µA, 10-4000 µA, 10-3000 µA, 10-2000 µA, optionally 20-1000 µA, optionally 20-500 µA, optionally 50-250 µA. In certain embodiments the electrical signal has a current of at least 10 µA, 20 µA, at least 50 µA, at least 60 µA, at least 70 µA, at least 80 µA, at least 90 µA, at least 100 µA, at least 110 µA, at least 150 µA, at least 180 µA, at least 200 µA, at least 220 µA, at least 250 µA, at least 300 µA, at least 400 µA, at least 500 µA, at least 600 µA, at least 700 µA, at least 800 µA, at least 900 µA, at least 1000 µA, at least 1200 µA, at least 1500 µA, at least 2000 µA, at least 3000 µA, at least 4000 µA, at least 5000 µA, at least 6000 µA, at least 7000 µA, at least 8000 µA. In certain embodiments, the electrical signal comprises a DC waveform and/or an AC waveform having a current of between 80 and 480 µA. In certain alternative embodiments, the electrical signal comprises a DC waveform and/or an AC waveform having a current of 8 mA.

Optogenetics is a technique that genetically modifies cells to express photosensitive features, which can then be activated with light to modulate cell function. Many different optogenetic tools have been developed that can be used to modulate neural firing. Mechanical forms of neuromodulation can include the use of ultrasound which may conveniently be implemented using external instead of implanted ultrasound transducers. Other forms of mechanical neuromodulation include the use of pressure (for example see "The effects of compression upon conduction in myelinated axons of the isolated frog sciatic nerve" by Robert Fern and P. J. Harrison Br. j. Anaesth. (1975), 47, 1123, which is incorporated herein by reference).

The techniques discussed above principally relate to the stimulation of neuronal activity. Where modulation by inhibition or blocking of neural activity or otherwise modifying activity in various ways is required, electrodes adjacent to or in contact with the nerve or particular parts of the nerve for example in contact with specific nerve fibres may be used to impart an electrical signal to inhibit activity in various ways, as would be appreciated by the skilled person.

In a third aspect, the invention provides a method of treating bronchoconstriction in a patient, for example bronchoconstriction-associated with COPD or asthma, the method comprising applying a signal to a part or all of a vagal nerve of said patient to stimulate neural activity in said nerve in the patient. In certain embodiments, the signal is applied to a cervical vagal nerve or a pulmonary branch of a vagal nerve.

In certain embodiments, the signal stimulates, preferably selectively stimulates, neural activity in afferent fibres of the vagal nerve. In certain preferred embodiments, the signal stimulates neural activity, preferably selectively stimulates neural activity, in afferent A fibres of the vagal nerve. In certain preferred embodiments the signal substantially selectively stimulates neural activity in afferent fibres of the vagal nerve. In certain preferred embodiments the signal substantially selectively stimulates neural activity in afferent A fibres of the vagal nerve.

In certain embodiments, the signal is applied by a neuromodulation device comprising one or more transducers configured to apply the signal. In certain preferred embodiments the neuromodulation device is at least partially implanted in the patient. In certain preferred embodiments, the neuromodulation device is wholly implanted in the patient.

In certain embodiments, the treatment of bronchoconstriction, for example COPD-associated or asthma-associated bronchoconstriction, is prophylactic treatment. That is, the methods of the invention reduce the frequency of bronchoconstriction episodes. In certain preferred such embodiments, the method prevents the onset of bronchoconstriction.

In certain embodiments, the treatment of bronchoconstriction, for example COPD-associated or asthma-associated bronchoconstriction, is therapeutic treatment. That is, the methods of the invention at least partially relieve or ameliorate the severity of a bronchoconstriction episode. In certain such embodiments, the methods of the invention wholly relieve a bronchoconstriction episode—that is, the episode is stopped by use of the method and the patient is able to breath normally.

In certain embodiments, treatment of bronchoconstriction, for example COPD-associated or asthma-associated bronchoconstriction, is indicated by an improvement in a measurable physiological parameter, for example a reduction in parasympathetic tone, an increase in sympathetic tone, a decrease in airway smooth muscle tone, an increase in blood oxygen saturation, a decrease in blood carbon dioxide concentration, an increase in mid-expiratory flow, an increase in expiration time, a decrease in respiratory rate, an increase in total lung capacity, an increase in forced expiration volume.

Suitable methods for determining the value for any given parameter would be appreciated by the skilled person.

In certain embodiments, treatment of the condition is indicated by an improvement in the profile of neural activity in the nerve or nerves to which the signal is applied. That is, treatment of the condition is indicated by the neural activity in the nerve(s) approaching the neural activity in a healthy individual—i.e. the pattern of action potentials in the nerve more closely resembling that exhibited by a healthy individual than before the intervention.

Stimulation of neural activity as a result of applying the signal is an increase in neural activity in the nerve or nerves to which the signal is applied. That is, in such embodiments, application of the signal results in the neural activity in at least part of the nerve or nerves to which the signal is applied (for example specific classes of nerve fibre in the nerve or nerves) being increased compared to the baseline neural activity in that part of the nerve. Such stimulation of neural activity could equally be across the whole nerve, in which case neural activity would be increased across the whole nerve or nerves. For the avoidance of doubt, stimulation of neural activity as used herein is taken to mean a functional increase in signalling activity in the indicated nerve or nerve fibres.

Therefore, in certain embodiments, the signal stimulates, preferably selectively stimulates, neural activity in afferent fibres of the vagal nerve. In certain preferred embodiments, the signal stimulates neural activity, preferably selectively stimulates neural activity, in afferent A fibres of the vagal nerve.

In certain embodiments, the signal is applied to the specified nerve on the left-side of the patient, the specified nerve on the right-side of the patient, or both. That is, in certain embodiments the signal is applied unilaterally or, alternatively, bilaterally.

In certain embodiments, the signal is applied intermittently. In certain such embodiments, the signal is applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments wherein the signal is applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the signal is applied intermittently, the signal is applied only when the patient is in a specific state. In certain such embodiments, the signal is applied only when the patient is in a state of bronchospasm. In such embodiments, the status of the patient (e.g. that they are experiencing bronchospasm) can be indicated by the patient. In alternative such embodiments, the status of the patient can be detected independently from any input from the patient. In certain embodiments in which the signal is applied by a neuromodulation device, the device further comprises a detector configured to detect the status of the patient, wherein the signal is applied only when the detector detects that the patient is in the specific state.

In certain embodiments of methods according to the invention, the method further comprises the step of detecting one or more physiological parameters of the patient, wherein the signal is applied only when the detected physiological parameter meets or exceeds a predefined threshold value. In such embodiments wherein more than one physiological parameter is detected, the signal may be applied when any one of the detected parameters meets or exceeds its threshold value, alternatively only when all of the detected parameters meet or exceed their threshold values. In certain embodiments wherein the signal is applied by a neuromodulation device, the device further comprises at least one detector element configured to detect the one or more physiological parameters.

In certain embodiments, the one or more detected physiological parameters are selected from: parasympathetic tone, sympathetic tone, ASM tone, blood oxygen saturation, blood carbon dioxide concentration, mid-expiratory flow, expiration time, respiratory rate, total lung capacity, and forced expiration volume.

Similarly, in certain embodiments the detected physiological parameter could be an action potential or pattern of action potentials in a nerve of the patient, for example a vagal nerve, optionally a cervical vagal nerve, or a pulmonary branch of the vagal nerve or afferent fibres thereof, wherein the action potential or pattern of action potentials is associated with bronchospasm.

It will be appreciated that any two or more of the indicated physiological parameters may be detected in parallel or consecutively. For example, in certain embodiments, the pattern of action potentials in the efferent fibres of a pulmonary branch of the vagal nerve can be detected at the same time as blood oxygen saturation.

In certain embodiments, the signal is permanently applied. That is, once begun, the signal is continuously applied to the nerve or nerves. It will be appreciated that in embodiments wherein the signal is a series of pulses, gaps between pulses do not mean the signal is not continuously applied.

In certain embodiments of the methods, the stimulation in neural activity caused by the application of the signal is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments, the stimulation of neural activity caused by the application of the signal is substantially persistent. That is, upon cessation of the signal, neural activity in the nerve or nerves remains substantially the same as when the signal was being applied—i.e. the neural activity during and following stimulation is substantially the same.

In certain embodiments, the stimulation of neural activity caused by the application of the signal is partially corrective, preferably substantially corrective. That is, upon cessation of the signal, neural activity in the nerve or nerves more closely resembles the pattern of action potentials observed in a healthy subject than prior to stimulation, preferably substantially fully resembles the pattern of action potentials observed in a healthy subject. For example, application of the signal stimulates neural activity, and upon cessation of the signal, the pattern of action potentials in the nerve or nerves resembles the pattern of action potentials observed in a healthy subject. It is hypothesised that such a corrective effect is the result of a positive feedback loop.

In certain such embodiments, once first applied, the signal may be applied intermittently or permanently, as described in the embodiments above.

In certain embodiments, the signal is applied to one or more cervical vagal nerves or pulmonary branches of a vagal nerve of said patient. In certain embodiments, the signal selectively stimulates afferent fibres, preferably afferent A fibres.

In certain embodiments, the signal is applied bilaterally. That is, in such embodiments, the signal is applied to a vagal nerve on both the left and right side of the patient such that neural activity is stimulated in the nerves to which the signal is applied—i.e. the stimulation is bilateral. In such embodiments, the signal applied to each nerve, and therefore the extent of stimulation, is independently selected from that applied to the other nerve or nerves. In certain embodiments the signal applied to the right nerve or nerves is the same as the signal applied to the left nerve or nerves. In certain alternative embodiments the signal applied to the right nerve or nerves is different to the signal applied to the left nerve or nerves.

In certain embodiments wherein the modulation is bilateral, each signal is applied by a neuromodulation device comprising one or more transducers for applying the signal. In certain such embodiments, all signals are applied by the same neuromodulation device, that device have at least two transducers, one to apply the signal to the left nerve(s) and one to apply the signal to the right nerve(s). In certain alternative embodiments, the each signal is applied by a separate neuromodulation device.

In certain embodiments, the signal applied is a non-destructive signal.

In certain embodiments of the methods according to the invention, the signal applied is an electrical signal, an electromagnetic signal (optionally an optical signal), a mechanical (optionally ultrasonic) signal, a thermal signal, a magnetic signal or any other type of signal.

In certain such embodiments in which more than one signal may be applied, for example when the modulation is bilateral, each signal may be independently selected from an electrical signal, an optical signal, an ultrasonic signal, and a thermal signal. In those such embodiments in which two signals are applied by one modulation device, the two signals may be the same type of signal or may be different types of signal independently selected from an electrical signal, an optical signal, an ultrasonic signal, and a thermal signal. In those embodiments in which two signals are applied, each by a separate neuromodulation device, the two signals may be the same type of signal or may be different types of signal independently selected from an electrical signal, an optical signal, an ultrasonic signal, and a thermal signal.

In certain embodiments in which the signal is applied by a neuromodulation device comprising at least one transducer, the transducer may be comprised of one or more electrodes, one or more photon sources, one or more ultrasound transducers, one more sources of heat, or one or more other types of transducer arranged to put the signal into effect.

In certain embodiments, the signal is an electrical signal, for example a voltage or current, and the transducer is an electrode, for example a wire electrode or a cuff electrode. In certain such embodiments the signal comprises a direct current (DC) waveform, such as a charge balanced DC waveform, or an alternating current (AC) waveform, or both a DC and an AC waveform.

In certain embodiments, the DC waveform or AC waveform may be a square, sinusoidal, triangular or complex waveform. The DC waveform may alternatively be a constant amplitude waveform. In certain embodiments the electrical signal is a DC square waveform of varying voltage.

In certain embodiments, the electrical signal is a DC waveform having a frequency in the range of 1 Hz-1 kHz, optionally 1-500 Hz, optionally 1-200 Hz, optionally 50-150 Hz, optionally 100 Hz.

In certain embodiments wherein the signal is an electrical signal, the electrical signal has a pulse duration of 0.005-0.1 ms, optionally 0.01-0.06 ms. optionally 0.01-0.05 ms, optionally 0.01-0.04 ms. In certain preferred embodiments the signal has a pulse duration of 0.01-0.03 ms, more preferably 0.01-0.02 ms.

In certain embodiments wherein the signal is an electrical signal the signal has a pulse duration of less than or equal to 0.1 ms, optionally less than or equal to 0.06 ms, optionally less than or equal to 0.05 ms, optionally less than or equal to 0.04 ms, optionally less than or equal to 0.03 ms, optionally less than or equal to 0.02 ms, optionally less than or equal to 0.01 ms. In certain preferred embodiments the signal has a pulse duration of 0.01 ms or 0.02 ms or 0.04 ms.

In certain preferred embodiments, the signal comprises a DC square waveform of 100 Hz, pulse duration 0.01 ms, or a DC square waveform of 100 Hz, pulse duration 0.02 ms. In certain other embodiments, the signal comprises a DC square waveform of at least 200 Hz, pulse duration 0.01 ms. In certain embodiments, the signal comprises a DC square waveform of 50-500 Hz, pulse duration 0.01 ms. In certain embodiments, the signal comprises a DC square waveform of between 20 and 200 Hz, pulse duration 0.01 ms.

It will be appreciated by the skilled person that the current amplitude of an applied electrical signal necessary to achieve the intended stimulation will depend upon the positioning of the electrode and the associated electrophysiological characteristics (e.g. impedance). It is within the ability of the skilled person to determine the appropriate current amplitude for achieving the intended stimulation in a given subject. For example, the skilled person is aware of methods suitable to monitor the neural activity profile induced by nerve stimulation. By further example, parameters that achieve selective afferent fibre stimulation will be indicated by bronchodilation being exhibited by the subject, for example by an increase in their EF50 and/or an increase in expiration time and/or a decrease in respiration rate, and/or an increase in forced expiration volume (FEV), and/or relaxation of the trachealis muscle. Selective stimulation of afferent A fibres in preference to Aδ fibres can be further indicated by more effective bronchodilation, and/or an absence of RAR activity-associated augmented breaths.

In certain embodiments, the electrical signal comprises a DC waveform and/or an AC waveform having a current of 1-8000 μA, 1-7000 μA, 1-6000 μA, 1-5000 μA, 1-4000 μA, 10-4000 μA, 10-3000 μA, 10-2000 μA, optionally 20-1000 μA, optionally 20-500 μA, optionally 50-250 μA. In certain embodiments the electrical signal has a current of at least 10 μA, 20 μA, at least 50 μA, at least 60 μA, at least 70 μA, at least 80 μA, at least 90 μA, at least 100 μA, at least 110 μA, at least 150 μA, at least 180 μA, at least 200 μA, at least 220 μA, at least 250 μA, at least 300 μA, at least 400 μA, at least 500 μA, at least 600 μA, at least 700 μA, at least 800 μA, at least 900 μA, at least 1000 μA, at least 1200 μA, at least 1500 μA, at least 2000 μA, at least 3000 μA, at least 4000 μA, at least 5000 μA, at least 6000 μA, at least 7000 μA, at least 8000 μA. In certain embodiments, the electrical signal comprises a DC waveform and/or an AC waveform having a current of between 80 and 480 μA. In certain alternative embodiments, the electrical signal comprises a DC waveform and/or an AC waveform having a current of 8 mA.

In certain embodiments wherein the signal is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In certain embodiments wherein the signal is a mechanical signal, the signal is an ultrasonic signal. In certain alternative embodiments, the mechanical signal is a pressure signal.

In certain embodiments, the method further comprises administration of a bronchodilator to the patient. In certain such embodiments, the bronchodilator is an anticholinergic compound (for example atropine or amfebutamone) or a beta-adrenoreceptor agonist (for example salbutamol).

In certain embodiments, the patient is refractory to bronchodilator treatment. That is, bronchodilator treatment is not in itself sufficient to fully treat bronchoconstriction in the patient. Therefore, stimulation of neural activity in a vagal nerve of the patient according to the invention provides an additional therapeutic option that may be used as an adjunct to or alternative to bronchodilator therapy. In certain such embodiments, the method of the invention further comprises administration of a bronchodilator to the patient. In certain such embodiments, the bronchodilator is an anticholinergic compound (for example atropine or amfebutamone) or a beta-adrenoreceptor agonist (for example salbutamol). In such embodiments, the method of the invention is expected to be an effective treatment due to a combinatorial effect. In certain embodiments, the patient is a patient suffering from "difficult asthma" or brittle asthma. Such patients may be refractory to bronchodilator therapy, for example when undergoing a severe asthma attack. Methods according to the invention are therefore expected to be particularly advantageous in such patients, providing an adjunct to or alternative to bronchodilator therapy.

In a fourth aspect, the invention provides a bronchodilator for use in a method of treating bronchoconstriction in a patient, wherein the method comprises:
  i. applying a signal to a vagal nerve of said patient to stimulate neural activity in said vagal nerve; and
  ii. administering the bronchodilator to the patient.

In certain embodiments, the bronchodilator for use in the method is an anticholinergic compound (for example atropine or amfebutamone) or a beta-adrenoreceptor agonist (for example salbutamol).

In certain embodiments, step (i) and step (ii) are applied substantially consecutively or, alternatively, the steps are applied concurrently. In certain embodiments, step (i) is performed before step (ii). In certain embodiments, step (ii) is performed before step (i).

In certain embodiments, the signal is applied to a cervical vagal nerve or a pulmonary branch of a vagal nerve. In certain embodiments the signal is applied to the afferent fibres of a vagal nerve.

In certain embodiments, the signal stimulates, preferably selectively stimulates, neural activity in afferent fibres of the vagal nerve. In certain preferred embodiments, the signal stimulates neural activity, preferably selectively stimulates neural activity, in afferent A fibres of the vagal nerve. In certain preferred embodiments the signal substantially selectively stimulates neural activity in afferent fibres of the vagal nerve. In certain preferred embodiments the signal substantially selectively stimulates neural activity in afferent A fibres of the vagal nerve.

In certain embodiments, the signal is applied by a neuromodulation device comprising one or more transducers configured to apply the signal. In certain preferred embodiments the neuromodulation device is at least partially implanted in the patient. In certain preferred embodiments, the neuromodulation device is wholly implanted in the patient.

In certain embodiments, the method of treatment of bronchoconstriction, for example COPD-associated or asthma-associated bronchoconstriction, is a prophylactic treatment. That is, the method of treatment reduces the frequency of bronchoconstriction episodes. In certain preferred such embodiments, the method prevents the onset of bronchoconstriction.

In certain embodiments, the treatment of bronchoconstriction, for example COPD-associated or asthma-associated bronchoconstriction, is therapeutic treatment. That is, the method of treatment at least partially relieves or ameliorates the severity of a bronchoconstriction episode. In certain such embodiments, the method wholly relieves a bronchoconstriction episode—that is, the episode is stopped and the patient is able to breathe normally.

In certain embodiments, treatment of bronchoconstriction, for example COPD-associated or asthma-associated bronchoconstriction, is indicated by an improvement in a measurable physiological parameter, for example a reduction in parasympathetic tone, an increase in sympathetic tone, a decrease in airway smooth muscle tone, an increase in blood oxygen saturation, a decrease in blood carbon dioxide concentration, an increase in mid-expiratory flow, an increase in expiration time, a decrease in respiratory rate, an increase in total lung capacity, an increase in forced expiration volume.

Suitable methods for determining the value for any given parameter would be appreciated by the skilled person.

In certain embodiments, treatment of the condition is indicated by an improvement in the profile of neural activity in the nerve or nerves to which the signal is applied. That is, treatment of the condition is indicated by the neural activity in the nerve(s) approaching the neural activity in a healthy individual—i.e. the pattern of action potentials in the nerve more closely resembling that exhibited by a healthy individual than before the intervention.

Stimulation of neural activity as a result of applying the signal is an increase in neural activity in the nerve or nerves to which the signal is applied. That is, in such embodiments, application of the signal results in the neural activity in at least part of the nerve or nerves to which the signal is applied (for example specific classes of nerve fibre in the nerve or nerves) being increased compared to the baseline neural activity in that part of the nerve. Such stimulation of neural activity could equally be across the whole nerve, in which case neural activity would be increased across the whole nerve or nerves. For the avoidance of doubt, stimulation of neural activity as used herein is taken to mean a functional increase in signalling activity in the indicated nerve or nerve fibres.

Therefore, in certain embodiments, the signal stimulates, preferably selectively stimulates, neural activity in afferent fibres of the vagal nerve. In certain preferred embodiments, the signal stimulates neural activity, preferably selectively stimulates neural activity, in afferent A fibres of the vagal nerve.

In certain embodiments, the signal is applied to the specified nerve on the left-side of the patient, the specified nerve on the right-side of the patient, or both. That is, in certain embodiments the signal is applied unilaterally or, alternatively, bilaterally.

In certain embodiments, the signal is applied intermittently. In certain such embodiments, the signal is applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments wherein the signal is applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the signal is applied intermittently, the signal is applied only when the patient is in a specific state. In certain such embodiments, the signal is applied only when the patient is in a state of bronchospasm. In such embodiments, the status of the patient (e.g. that they are experiencing bronchospasm) can be indicated by the patient. In alternative such embodiments, the status of the patient can be detected independently from any input from the patient. In certain embodiments in which the signal is applied by a neuromodulation device, the device further comprises a detector configured to detect the status of the patient, wherein the signal is applied only when the detector detects that the patient is in the specific state.

In certain embodiments of the fourth aspect, the bronchodilator is for use in a method of treatment further comprising the step of detecting one or more physiological parameters of the patient, wherein the signal is applied only when the detected physiological parameter meets or exceeds a predefined threshold value. In such embodiments wherein more than one physiological parameter is detected, the signal may be applied when any one of the detected parameters meets or exceeds its threshold value, alternatively only when all of the detected parameters meet or exceed their threshold values. In certain embodiments wherein the signal is applied by a neuromodulation device, the device further comprises at least one detector element configured to detect the one or more physiological parameters.

In certain embodiments, the one or more detected physiological parameters are selected from: parasympathetic tone, sympathetic tone, ASM tone, blood oxygen saturation, blood carbon dioxide concentration, mid-expiratory flow, expiration time, respiratory rate, total lung capacity, and forced expiration volume.

Similarly, in certain embodiments the detected physiological parameter could be an action potential or pattern of action potentials in a nerve of the patient, for example a vagal nerve, optionally a cervical vagal nerve, or a pulmonary branch of the vagal nerve or afferent fibres thereof, wherein the action potential or pattern of action potentials is associated with bronchospasm.

It will be appreciated that any two or more of the indicated physiological parameters may be detected in parallel or consecutively. For example, in certain embodiments, the pattern of action potentials in the efferent fibres of a pulmonary branch of the vagal nerve can be detected at the same time as blood oxygen saturation.

In certain embodiments, the signal is permanently applied. That is, once begun, the signal is continuously applied to the nerve or nerves. It will be appreciated that in embodiments wherein the signal is a series of pulses, gaps between pulses do not mean the signal is not continuously applied.

In certain embodiments, the stimulation in neural activity caused by the application of the signal is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments, the stimulation of neural activity caused by the application of the signal is substantially persistent. That is, upon cessation of the signal, neural activity in the nerve or nerves remains substantially the same as when the signal was being applied—i.e. the neural activity during and following stimulation is substantially the same.

In certain embodiments, the stimulation of neural activity caused by the application of the signal is partially corrective, preferably substantially corrective. That is, upon cessation of the signal, neural activity in the nerve or nerves more closely resembles the pattern of action potentials observed in a healthy subject than prior to stimulation, preferably substantially fully resembles the pattern of action potentials observed in a healthy subject. For example, application of the signal stimulates neural activity, and upon cessation of the signal, the pattern of action potentials in the nerve or nerves resembles the pattern of action potentials observed in a healthy subject. It is hypothesised that such a corrective effect is the result of a positive feedback loop.

In certain such embodiments, once first applied, the signal may be applied intermittently or permanently, as described in the embodiments above.

In certain embodiments, the signal is applied to one or more cervical vagal nerves or pulmonary branches of a vagal nerve of said patient. In certain embodiments, the signal selectively stimulates afferent fibres of the nerve, preferably afferent A fibres of the nerve.

In certain embodiments, the signal is applied bilaterally. That is, in such embodiments, the signal is applied to a vagal nerve on both the left and right side of the patient such that neural activity is stimulated in the nerves to which the signal is applied—i.e. the stimulation is bilateral. In such embodiments, the signal applied to each nerve, and therefore the extent of stimulation, is independently selected from that applied to the other nerve or nerves. In certain embodiments the signal applied to the right nerve or nerves is the same as the signal applied to the left nerve or nerves. In certain alternative embodiments the signal applied to the right nerve or nerves is different to the signal applied to the left nerve or nerves.

In certain embodiments wherein the modulation is bilateral, each signal is applied by a neuromodulation device comprising one or more transducers for applying the signal. In certain such embodiments, all signals are applied by the same neuromodulation device, that device have at least two transducers, one to apply the signal to the left nerve(s) and one to apply the signal to the right nerve(s). In certain alternative embodiments, the each signal is applied by a separate neuromodulation device.

In certain embodiments, the signal applied is a non-destructive signal.

In certain embodiments, the signal applied is an electrical signal, an electromagnetic signal (optionally an optical signal), a mechanical (optionally ultrasonic) signal, a thermal signal, a magnetic signal or any other type of signal.

In certain such embodiments in which more than one signal may be applied, for example when the modulation is bilateral, each signal may be independently selected from an electrical signal, an optical signal, an ultrasonic signal, and a thermal signal. In those such embodiments in which two signals are applied by one modulation device, the two signals may be the same type of signal or may be different types of signal independently selected from an electrical signal, an optical signal, an ultrasonic signal, and a thermal signal. In those embodiments in which two signals are applied, each by a separate neuromodulation device, the two signals may be the same type of signal or may be different types of signal independently selected from an electrical signal, an optical signal, an ultrasonic signal, and a thermal signal.

In certain embodiments in which the signal is applied by a neuromodulation device comprising at least one transducer, the transducer may be comprised of one or more electrodes, one or more photon sources, one or more ultrasound transducers, one more sources of heat, or one or more other types of transducer arranged to put the signal into effect.

In certain embodiments, the signal is an electrical signal, for example a voltage or current, and the transducer is an electrode, for example a wire electrode or a cuff electrode. In certain such embodiments the signal comprises a direct current (DC) waveform, such as a charge balanced DC waveform, or an alternating current (AC) waveform, or both a DC and an AC waveform.

In certain embodiments, the DC waveform or AC waveform may be a square, sinusoidal, triangular or complex waveform. The DC waveform may alternatively be a constant amplitude waveform. In certain embodiments the electrical signal is a DC square waveform of varying voltage.

In certain embodiments, the electrical signal is a DC waveform having a frequency in the range of 1 Hz-1 kHz, optionally 1-500 Hz, optionally 1-200 Hz, optionally 50-150 Hz, optionally 100 Hz.

In certain embodiments wherein the signal is an electrical signal, the electrical signal has a pulse duration of 0.005-0.1 ms, optionally 0.01-0.06 ms. optionally 0.01-0.05 ms, optionally 0.01-0.04 ms. In certain preferred embodiments the signal has a pulse duration of 0.01-0.03 ms, more preferably 0.01-0.02 ms.

In certain embodiments wherein the signal is an electrical signal the signal has a pulse duration of less than or equal to 0.1 ms, optionally less than or equal to 0.06 ms, optionally less than or equal to 0.05 ms, optionally less than or equal to 0.04 ms, optionally less than or equal to 0.03 ms, optionally less than or equal to 0.02 ms, optionally less than or equal to 0.01 ms. In certain preferred embodiments the signal has a pulse duration of 0.01 ms or 0.02 ms or 0.04 ms.

In certain preferred embodiments, the signal comprises a DC square waveform of 100 Hz, pulse duration 0.01 ms, or a DC square waveform of 100 Hz, pulse duration 0.02 ms. In certain other embodiments, the signal comprises a DC square waveform of at least 200 Hz, pulse duration 0.01 ms. In certain embodiments, the signal comprises a DC square waveform of 50-500 Hz, pulse duration 0.01 ms. In certain embodiments, the signal comprises a DC square waveform of between 20 and 200 Hz, pulse duration 0.01 ms.

It will be appreciated by the skilled person that the current amplitude of an applied electrical signal necessary to achieve the intended stimulation will depend upon the positioning of the electrode and the associated electrophysiological characteristics (e.g. impedance). It is within the ability of the skilled person to determine the appropriate current amplitude for achieving the intended stimulation in a given subject. For example, the skilled person is aware of methods suitable to monitor the neural activity profile induced by nerve stimulation. By further example, parameters that achieve selective afferent fibre stimulation will be indicated by bronchodilation being exhibited by the subject, for example by an increase in their EF50 and/or an increase in expiration time and/or a decrease in respiration rate, and/or an increase in forced expiration volume (FEV), and/or relaxation of the trachealis muscle. Selective stimulation of afferent A fibres in preference to Aδ fibres can be further indicated by more effective bronchodilation, and/or an absence of RAR activity-associated augmented breaths.

In certain embodiments, the electrical signal comprises a DC waveform and/or an AC waveform having a current of 1-8000 µA, 1-7000 µA, 1-6000 µA, 1-5000 µA, 1-4000 µA, 10-4000 µA, 10-3000 µA, 10-2000 µA, optionally 20-1000 µA, optionally 20-500 µA, optionally 50-250 µA. In certain embodiments the electrical signal has a current of at least 10 µA, 20 µA, at least 50 µA, at least 60 µA, at least 70 µA, at least 80 µA, at least 90 µA, at least 100 µA, at least 110 µA, at least 150 µA, at least 180 µA, at least 200 µA, at least 220 µA, at least 250 µA, at least 300 µA, at least 400 µA, at least 500 µA, at least 600 µA, at least 700 µA, at least 800 µA, at least 900 µA, at least 1000 µA, at least 1200 µA, at least 1500 µA, at least 2000 µA, at least 3000 µA, at least 4000 µA, at least 5000 µA, at least 6000 µA, at least 7000 µA, at least 8000 µA. In certain embodiments, the electrical signal comprises a DC waveform and/or an AC waveform having a current of between 80 and 480 µA. In certain alternative embodiments, the electrical signal comprises a DC waveform and/or an AC waveform having a current of 8 mA.

In certain embodiments, the patient is refractory to bronchodilator treatment. That is, bronchodilator treatment is not in itself sufficient to treat the bronchoconstriction. Therefore, use of the bronchodilator in conjunction with stimulation of neural activity in a vagal nerve of the patient is expected to be an effective treatment due to the combinatorial effect. In certain embodiments, the patient is a patient suffering from "difficult asthma" or brittle asthma.

In a fifth aspect, the invention provides a neuromodulatory electrical waveform for use in treating bronchoconstriction, for example COPD-associated or asthma-associated bronchoconstriction, in a patient, wherein the waveform is an direct current (DC) waveform having a frequency of 1-1000 Hz, such that, when applied to a vagal nerve, of the patient, the waveform stimulates neural signalling in the nerve, preferably selectively stimulating neural activity in the afferent fibres of the nerve, more preferably selectively stimulating neural activity in the afferent A fibres. In certain embodiments, the waveform, when applied to the nerve, relieves or prevents bronchoconstriction. For the avoidance of doubt, stimulation of neural activity as used herein is taken to mean a functional increase in signalling activity in the indicated nerve or nerve fibres.

In a sixth aspect, the invention provides use of a neuromodulation device for treating bronchoconstriction, in particular COPD-associated or asthma-associated bronchoconstriction in a patient by stimulating neural activity in a vagal nerve of the patient, preferably a cervical vagal nerve or a pulmonary branch of the vagal nerve, more preferably the afferent fibres of said vagal nerve, more preferably the afferent A fibres of said vagal nerve. For the avoidance of doubt, stimulation of neural activity as used herein is taken to mean a functional increase in signalling activity in the indicated nerve or nerve fibres.

In a seventh aspect is provided a bronchodilator for use in treating bronchoconstriction in a patient, the patient having a device according to the first aspect implanted.

In certain embodiments, the bronchodilator for use in in treating bronchoconstriction is an anticholinergic compound (for example atropine or amfebutamone) or a beta-adrenoreceptor agonist (for example salbutamol).

In certain embodiments, the treatment of bronchoconstriction, for example COPD-associated or asthma-associated bronchoconstriction, is a prophylactic treatment. That is, the treatment reduces the frequency of bronchoconstriction episodes. In certain preferred such embodiments, the treatment prevents the onset of bronchoconstriction.

In certain embodiments, the treatment of bronchoconstriction, for example COPD-associated or asthma-associated bronchoconstriction, is therapeutic treatment. That is, the treatment at least partially relieves or ameliorates the severity of a bronchoconstriction episode. In certain such embodiments, the treatment wholly relieves a bronchoconstriction episode—that is, the episode is stopped and the patient is able to breathe normally.

In certain embodiments, treatment of bronchoconstriction, for example COPD-associated or asthma-associated bronchoconstriction, is indicated by an improvement in a measurable physiological parameter, for example a reduction in parasympathetic tone, an increase in sympathetic tone, a decrease in airway smooth muscle tone, an increase in blood oxygen saturation, a decrease in blood carbon dioxide concentration, an increase in mid-expiratory flow, an increase in expiration time, a decrease in respiratory rate, an increase in total lung capacity, an increase in forced expiration volume.

Suitable methods for determining the value for any given parameter would be appreciated by the skilled person.

In certain embodiments, treatment of the condition is indicated by an improvement in the profile of neural activity in the nerve or nerves to which the signal is applied. That is, treatment of the condition is indicated by the neural activity in the nerve(s) approaching the neural activity in a healthy individual—i.e. the pattern of action potentials in the nerve more closely resembling that exhibited by a healthy individual than before the intervention.

In certain embodiments, the patient is refractory to bronchodilator treatment. That is, bronchodilator treatment is not in itself sufficient to treat the bronchoconstriction. Therefore, use of the bronchodilator in conjunction with a device according to the first aspect is expected to be an effective treatment due to the combinatorial effect. In certain embodiments, the patient is a patient suffering from "difficult asthma" or brittle asthma.

In an eighth aspect is a neuromodulation system, the system comprising a plurality of devices according to the first aspect. In such a system, each device may be arranged to communicate with at least one other device, optionally all devices in the system. In certain embodiments, the system is arranged such that, in use, the devices are positioned to bilaterally modulate the neural activity of the afferent fibres of the vagal nerves of a patient.

In such embodiments, the system may further comprise additional components arranged to communicate with the apparatuses of the system, for example a processor, a data input facility, a and/or a data display module. In certain such embodiments, the system further comprises a processor. In certain such embodiments, the processor is comprised within a mobile device (for example a smart phone) or computer.

In a preferred embodiment of all aspects of the invention, the subject or patient is a mammal, more preferably a human.

In a preferred embodiment of all aspects of the invention, the signal or signals is/are applied substantially exclusively to the nerves specified, and not to other nerves.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

In Vitro Methods:

Compound Action Potential Recordings:

Naive male Sprague-Dawley rats were euthanized via $CO_2$ asphyxiation according to IACUC approved protocols. Left or right vagi, spanning 30-40 mm from the nodose and jugular ganglia to the subclavian arteries, were removed for processing along with the carotid artery. Tissue was assayed and processed in Krebs-Henseleit buffer (mM): NaCl (113.0), KCl (4.8), $CaCl_2$ (2.5), $KH_2PO_4$ (1.2), $MgSO_4$ (1.2), $NaHCO_3$ (25.0), dextrose (5.55), equilibrated with 95% $O_2$: 5% $CO_2$. Under dissection microscopes, the vagus was separated from the carotid artery, connective tissue, and fat and partially de-sheathed. Tissue was transferred and mounted to a pre-greased water-jacketed marsh ganglion bath (type 858, Harvard Apparatus, Holliston, MA, U.S.A.) with surgical silk (5.0). All chambers were filled with fresh assay buffer and allowed to equilibrate for 30-60 min at 35-37° C. prior to recording.

Stimulation was performed on the cervical vagus with platinum hook electrodes or 300 μm platinum/iridium silicone cuff electrodes (CorTec GmbH, Freiberg, Germany). Stimuli of varying frequency, pulse duration (PD), and voltage were generated with a square-pulse stimulator (Grass model S48; Natus Neurology Inc., Warwick, RI, U.S.A.) and isolated from ground with a transformer stimulus isolation unit (Grass model SIU5; Natus Neurology Inc., Warwick, RI, U.S.A.)). The anode was oriented distally. Voltage was measured across a 100Ω resistor in series with the electrodes to calculate current output. Compound action potentials were recorded on the proximal vagus with a microelectrode AC amplifier (A-M Systems model 1800, Carlsborg, WA, U.S.A.) using Ag/AgCl hook electrodes. Differential signals were filtered with a low cut-off frequency of 10 Hz and high cut-off frequency of 1 kHz. Tissue was grounded via an Ag/AgCl hook electrode half way between the stimulating cathode and recording electrodes. After checking viability of tissue, baths were drained and rapidly filled with pre-warmed mineral oil and recording commenced.

Analog signals were digitized at 10 kHz using an analog-to-digital converter (Power1401 625 kHz; Cambridge Electronic Design Ltd., Cambridge, England, UK) and Spike 2 software (v5.21, Cambridge Electronic Design Ltd). Non-linear regressions performed in Graphpad Prism (v5.03, GraphPad Software, San Diego California USA).

Threshold current strength/duration plots were fit to:

$$I_{threshold} = I_{rheobase}/(1-e^{-PD/\tau}),$$

Where Chronaxie=ln2*τ

Current response curves for individual fiber groups at select pulse durations were normalized and plotted vs. logarithmic converted current. Results were fit to a 4-parameter sigmoidal curve with top and bottom constrained to 100 and 0, respectively and a shared slope for comparator data sets. The percentage of A fibers activated at 10% Aδ fiber recruitment is reported as well as current required to recruit a 50% response (I50).

Tracheal Contraction Studies

Naive male Sprague-Dawley rats were euthanized via $CO_2$ asphyxiation according to IACUC approved protocols. Tissue was assayed and processed in Krebs-Henseleit buffer (mM): NaCl (113.0), KCl (4.8), $CaCl_2$ (2.5), $KH_2PO_4$ (1.2), $MgSO_4$ (1.2), $NaHCO_3$ (25.0), dextrose (5.55), equilibrated with 95% $O_2$: 5% $CO_2$.

The right vagus with the vagal ganglia along with the right carotid artery, trachea (with some larynx), esophagus, heart, and lungs were removed en bloc. Under microscopes the preparation was processed so that only the vagus intact with the trachea (larynx to first bifurcation) remained, denuded of connective tissue and fat and partially de-sheathed. Care was taken to remove the subclavian artery and the esophagus while leaving the recurrent laryngeal nerve intact with both the vagus and the trachea. Lung, heart and aorta where carefully removed as to not damage the vagus innervations to the trachea. The trachea was then cut open opposite the smooth muscle and flushed with KREBS buffer.

Tissue was transferred and mounted to a custom two-chamber perfused tissue bath. The nodose ganglia was fed into the smaller chamber through a inter-bath opening and sealed with grease with the distal vagus and trachea in the larger bath. On the left side of the trachea, a small strip (2 cartilage rings) was cut to the smooth muscle and tied with surgical silk (5.0) to a pre-calibrated force transducer (Grass Force-displacement transducer FT03, Natus Neurology Inc., Warwick, RI, U.S.A) connected to an strain gauge amplifier (Grass AC/DC strain gauge amplifier Model P122, Natus Neurology Inc., Warwick, RI, U.S.A). Basal tension was set to 1.5-2 g. All chambers were filled with fresh assay buffer and allowed to equilibrate for 30-60 min at 35-37° C. prior to recording.

Paired compound action potential recordings on the proximal cervical vagus were performed as described in "Compound Action Potential Recordings". Contraction stimulus was applied in 0.8 Hz trains of 350 msec to replicate respiration in a rat. Pulse frequency ranged from 10-100 Hz.

Current response curves for individual fiber groups and contractions at select pulse durations were normalized and plotted vs. logarithmic converted current. Results were fit to a 4-parameter sigmoidal curve.

In Vitro Results

Wave Characteristics

Electrical excitation of rat left vagus (35° C.) utilizing a CorTec micro cuff resulted in the generation of three distinct compound action potential waves consistent with those reported in literature (Woodbury D. and Woodbury J., Effects of vagal stimulation on experimentally induced seizures in rats. Epilepsia 31 (1990) 7-19; Erlanger J, Gasser H S. The action potential in fibers of slow conduction in spinal roots and somatic nerves. Am J Physiol 1930; 92:43-82; Mollet L, et al. Electrophysiological responses from vagus nerve stimulation in rats. Int J Neural Syst. 2013 December; 23(6):1350027; Carr M J, Undem B J. Bronchopulmonary afferent nerves. Respirology. 2003 September; 8(3):291-301, each of which is incorporated herein by reference in its entirety).

Waves are designated A, Aδ and C according to standard afferent sensory fiber nomenclature, with Aδ fibers corresponding/overlapping with B fibers referenced in some literature sources (Mollet L, et al. and; Carr M J, Undem B J., op. cit.). The observed myelinated A-fiber conduction velocity ranged from 66.7 to 8.8 m/s with an average peak velocity of 30.6 m/s while Aδ-fiber conduction velocity ranged from 13.7 to 4.1 m/s with an average peak velocity of 6.6 m/s. Activation of un-myelinated C-fiber yielded two distinct peaks within a single wave, conduction velocity ranged from 1.3 to 0.5 m/s with average peak velocities of 1.0 and 0.7 m/s. Double peaked C-waves in rat have previously been described by Woodbury and Woodbury (1990). An exemplar trace is shown in FIG. 1.

Strength/Duration Curve

Current threshold strength/duration plots are shown in FIG. 3. Afferent A-fibres and Aδ-fibres possess similar chronaxie at 0.044 msec (95% CI: 0.025 to 0.062) and 0.047 msec (95% CI: 0.028 to 0.067), respectively. Threshold Aδ/A ratios are approximately 3-fold across all pulse durations. At the smallest PD tested (0.01 msec), Aδ/A ratio is 3.04 (Aδ-fiber threshold: 164 μA, A-fiber threshold: 54 μA), whereas on the other end of the spectrum, the rheobase for A- and Aδ-fibers is calculated as 8.2 μA (95% CI: 5.3 to 11.1) and 22.6 μA (95% CI: 14.7 to 30.4), respectively, with an Aδ/A ratio of 2.75. This is graphically demonstrated in FIG. 3C with ordinates converted to a log scale resulting in parallel and offset curve fits for A- and Aδ-fiber thresholds. C-fiber chronaxie and rheobase are calculated as 0.088 msec (95% CI: 0.011 to 0.166) and 139 μA (95% CI: 30.0 to 248.6), respectively. The two peaks within the C-wave were concurrent; therefore a single threshold is reported. In all cases thresholds were discernible from noise at about 5-10% of the maximal response.

Current Response Curves (IRC) with CorTec Cuff 300 um

IRCs, FIG. 4, spanned from sub- to supra-maximal stimuli for 0.01 and 0.02 msec pulse durations (PD). A- and Aδ-fibers with 0.01 msec pulse durations had $I_{50}$ s of 82 μA (95% CI: 72.5-91.8 μA) and 238 μA (95% CI: 215-264 μA), respectively. On average, with a 0.01 msec PD, 79% (95% CI: 72-86%) of A-fibers have been activated prior to engagement of 10% of the Aδ-fibers. When increasing PD to 0.02 msec, the selectivity window remains (88% (95% CI: 82-95%) of A- at 10% Aδ-fibers) despite a leftward shift in $I_{50}$ for both A- (47 μA (95% CI: 43-52 μA) and Aδ-fibers 136 μA (95% CI: 123-151 μA)).

Tracheal Contraction Studies

In paired studies, FIG. 5, vagally induced parasympathetic efferent contractions (0.01 msec $I_{50}$: 1.62 mA (95% CI: 1.32-1.99 mA), 0.2 msec $I_{50}$: 169 μA (95% CI: 139-205 μA,) of the trachea accumulate at currents above those required for Aδ-fiber activation (0.01 msec $I_{50}$: 437 μA (95% CI: 364-524 μA), 0.2 msec $I_{50}$: 94 μA (95% CI: 78.4-113 μA,) but below those required for C-fibers (0.2 msec $I_{50}$: 364 μA (95% CI: 314-421 μA,) for both 0.01 and 0.2 msec PD. A-fibers are fully activated (0.01 msec $I_{50}$: 124 μA (95% CI: 108-142 μA), 0.2 msec $I_{50}$: 23.3 μA (95% CI: 20.3-26.8 μA,) prior to parasympathetic efferent contraction accumulation.

In Vivo Methods

Tracheal Cannulation and Electrode Placement in the Rat

Young male Sprague-Dawley rats (360-422 g) were anesthetized with urethane (1.2 g/kg i.p.) and supplemental doses were given to abolish the withdrawal reflex. The animals were placed on a heating pad to help maintain normal body temperature. A tracheal cannula was placed via a tracheostomy and attached to heated pneumotachograph (model 8420B; Hans Rudolph Inc., Shawnee, KS, U.S.A.), through which the animal breathed spontaneously. The pressure difference across the pneumotachograph was measured using a differential pressure transducer (MP45-14; Validyne Engineering Corp.; Northridge, CA, U.S.A.) to produce a respiratory flow signal. The analog signal was digitized at 100 Hz using an analog-to-digital converter (Power1401; Cambridge Electronic Design Ltd., Cambridge, England, UK) and integrated to produce tidal volume using Spike2 software (Cambridge Electronic Design Ltd). The flow and volume signals were used to derive respiratory parameters on a breath-by-breath basis including mid-expiratory flow ($EF_{50}$), which is an index of bronchial tone, using Spike2 software. The respiratory flow signal was calibrated each experimental day.

A surgical approach was made to access the cervical vagus nerves. A custom-made bipolar cuff electrode (CorTec GmbH, Freiberg, Germany) was placed on right vagus nerve. The nerve was electrically stimulated using a square-pulse stimulator (Grass model S48; Natus Neurology Inc., Warwick, RI, U.S.A.) attached to a stimulus isolation unit (Model 2200; A-M Systems, Carlsborg, WA, U.S.A.) to deliver constant current.

Sonomicrometer Crystal Implantation and Electrode Placement in the Dog

Mongrel dogs (24.8-28.5 kg) were premedicated with diazepam. Anesthesia was induced and maintained using ketamine and dexmedetomidine. Temperature was maintained with the help of a circulating water blanket. The trachea was intubated per os. Dogs breathed spontaneously or were artificially ventilated (10-20 mL/kg, 8-30 breaths/min). Surgical sites at the cervical and inguinal areas were clipped, prepared and draped. A venous catheter was placed in the femoral vein for administration of drugs. Arterial catheters were placed in the femoral and/or carotid artery for direct hemodynamic and cardiac measurements and blood sampling for blood gas analysis.

A ~12 cm incision was made in the medial or right lateral cervical region. Approximately 6 cm of the carotid sheath was opened by dissection to isolate the vagus nerve. Up to three cuff electrodes (CorTec GmbH, Freiberg, Germany) were placed onto each vagus nerve. The trachea was reflected to expose the trachealis muscle. Care was taken to avoid disrupting the recurrent laryngeal innervation to the trachea. Two small 1-2 mm incisions were made in the fascia covering the trachealis muscle, one near each insertion to the tracheal cartilage, at the level of mid extrathoracic trachea or distal. A ~2 mm pocket in the trachealis was formed by dissection. A 1-mm diameter sonomicrometry crystal (Sonometrics Corp., London, Ontario, Canada) was placed in each pocket and sutured closed to fully embed the crystal. Up to two pairs of sonomicrometry crystals were placed.

The nerve was electrically stimulated using a square-pulse stimulator (Grass model S48; Natus Neurology Inc., Warwick, RI, U.S.A.) attached to a stimulus isolation unit (Model 2200; A-M Systems, Carlsborg, WA, U.S.A.) to deliver constant current. Sonomicrometry crystal leads were attached to an amplifier (Universal Dimension Gauge, Sonometrics Corp., London, Ontario, Canada) and the signal was displayed on an oscilloscope (Tektronix, Inc., Beaverton, OR, U.S.A). Data were digitized and analyzed using Power 1401 amplifier (Cambridge Electronic Design Ltd., Cambridge, England) running Spike2 software (Cambridge Electronic Design Ltd., Cambridge, England).

Electrical Stimulus Parameters

For the rat, pulse width was set at 0.01 ms. Stimulation rate was set between 50-500 Hz, and current amplitude was set between 80 and 480 µA. For the dog, pulse width was set at 0.01 ms, stimulation rate was set between 20 and 200 Hz, and current amplitude was set between 100 µA and 16 mA. Duration of the stimulus was up to 2 min.

Data Analysis

The mid-expiratory flow (EF50, e.g. FIG. 6) values of 40 consecutive breaths preceding the electrical stimulation were averaged and compared with the average of 40 consecutive breaths obtained 60 s after the onset of the stimulus. Expiratory time (TE) values were the averaged five breaths after the stimulus onset. Statistical comparisons were made using a paired t-test. A P-value<0.05 was considered significant.

Results

Electrical stimulation to the cervical right vagus nerve elicited an increase in EF50 that reach a plateau approximately one min after stimulus onset and was sustained for the duration of the stimulation (FIG. 7A). The electrical stimulation also prolonged expiratory time ($T_E$), which was longest immediately after the onset of stimulation and shortened over the next 30 s and reached a plateau for the duration of the stimulation (FIG. 7B). Data from the rat revealed that effective dose producing 50% change in expiratory time is dependent on frequency as assessed using right vagus stimulation, with maximal change observed at 200 Hz and above (FIG. 8; n=3). Group data revealed that the sustained EF50 (31.5±20.6 mL/s) was significantly greater than baseline (24.4±14.9 mL/s; FIG. 9A; P<0.05, n=6). $T_E$ over the same period (0.57±0.09 s) was also significantly greater than in baseline (0.39±0.08 s; FIG. 9B; P<0.01; n=6). At higher current amplitude stimulation, augmented breaths were elicited, which is consistent with the activation of afferent Aδ fibers (FIG. 10). Using sonomicrometry to directly measure tracheal dimensions, bilateral stimulation of the vagus in the dog elicited a relaxation of the trachea (FIG. 11A) in similar fashion as that of atropine (FIG. 11B).

The invention claimed is:

1. A method of treating bronchoconstriction in a patient, the method comprising:
    applying an electrical signal by a neuromodulation device partially implanted in the patient and positioned in signaling contact with a pulmonary branch of a vagal nerve of the patient, wherein the neuromodulation device comprises one or more electrodes that apply the electrical signal to afferent A fibers of the vagal nerve of said patient to selectively stimulate neural activity in the afferent A fibers of the vagal nerve in said patient, while not stimulating efferent fibers or afferent Aδ fibers, wherein the electrical signal—has a frequency in the range of 50-150 Hz, and wherein the electrical signal has a pulse duration of 0.005-0.1 ms, such that the electrical signal to the vagal nerve produces an improvement in a physiological parameter indicative of treating bronchoconstriction in the patient,
    providing a detector for detecting the physiological parameter; and
    measuring the physiological parameter, wherein the physiological parameter is airway smooth muscle (ASM) tone, blood oxygen saturation, blood carbon dioxide concentration, tidal mid-expiratory flow, respiratory rate, total lung capacity, or forced expiration volume;
    wherein the improvement in the physiological parameter is a decrease in airway smooth muscle tone, an increase in blood oxygen saturation, a decrease in blood carbon dioxide concentration, an increase in tidal mid-expiratory flow, a decrease in respiratory rate, an increase in total lung capacity, or an increase in forced expiration volume, from an initial measurement.

2. A method according to claim 1, wherein the electrical signal has a pulse duration of 0.01-0.06 ms.

3. A method according to claim 1, wherein the electrical signal has a current of 1-8000 µA.

4. A method according to claim 1, wherein the electrical signal is applied only when the measured physiological parameter meets or exceeds a predefined threshold value.

5. A method according to claim 1, wherein the method of treating bronchoconstriction is a method of treating asthma or COPD.

6. The method according to claim 1, wherein applying the electrical signal further comprises an intermittent signaling wherein the electrical signal is applied for a first time period, stopped for a second time period, reapplied for a third time period, and stopped for a fourth time period.

7. The method according to claim 6, wherein the first time period, second time period, third time period, and fourth time period run sequentially and consecutively.

8. The method of claim 1, wherein the signal is applied for one or more time periods between 5 seconds and 24 hours.

9. A method according to claim 1, wherein the electrical signal has a pulse duration of 0.01-0.05 ms.

10. A method according to claim 1, wherein the electrical signal has a pulse duration of 0.01-0.04 ms.

11. A method according to claim 1, wherein the electrical signal has a pulse duration of 0.01-0.03 ms.

12. A method of treating a bronchoconstriction in a patient, wherein the method comprises:
    i. applying a signal to a pulmonary branch of a vagal nerve of said patient to selectively stimulate neural activity in afferent A fibers, while not stimulating efferent fibers or afferent Aδ fibers, of the vagal nerve, wherein the signal is applied by a neuromodulation device partially implanted in the patient and positioned in signaling contact with the vagal nerve, the neuromodulation device comprising one or more transducers configured to apply the signal, wherein the signal has a frequency of 50-150 Hz, and wherein the signal has a pulse duration of 0.05-0.1 ms, such that the signal to the vagal nerve produces an improvement in a physiological parameter indicative of treating bronchoconstriction in the patient;
    ii. providing a detector for detecting the physiological parameter;
    iii. administering a bronchodilator to the patient; and
    iv. measuring the physiological parameter, wherein the physiological parameter is airway smooth muscle (ASM) tone, blood oxygen saturation, blood carbon dioxide concentration, tidal mid-expiratory flow, respiratory rate, total lung capacity, or forced expiration volume;
    wherein the improvement in the physiological parameter is a decrease in airway smooth muscle tone, an increase in blood oxygen saturation, a decrease in blood carbon dioxide concentration, an increase in tidal mid-expiratory flow, a decrease in respiratory rate, an increase in total lung capacity, or an increase in forced expiration volume, from an initial measurement.

13. The method of claim 12, wherein the signal is applied for one or more time periods.

14. The method of claim 13, wherein applying the signal further comprises an intermittent signaling wherein the signal is applied for a first time period, stopped for a second time period, reapplied for a third time period, and stopped for a fourth time period.

15. A system for stimulating neural activity in a vagal nerve of a patient to treat bronchoconstriction in the patient, the system comprising:
    at least one transducer, configured to be in signaling contact with a pulmonary branch of a vagal nerve, the at least one transducer configured to be at least partially implanted in the patient; and
    a voltage or current source configured to generate a signal to be selectively applied to afferent A fibers of the vagal nerve of the patient, while not stimulating efferent fibers or afferent Aδ fibers, via the at least one transducer, wherein the signal has a frequency of 50-150 Hz, and wherein the signal has a pulse duration of between 0.005 and 0.1 ms, such that the signal to the vagal nerve produces an improvement in a physiological parameter indicative of treating bronchoconstriction in the patient, wherein the system further comprises a detector for detecting the physiological parameter, and
    wherein the improvement in the physiological parameter is a decrease in airway smooth muscle tone, an increase in blood oxygen saturation, a decrease in blood carbon dioxide concentration, an increase in tidal mid-expiratory flow, a decrease in respiratory rate, an increase in total lung capacity, or an increase in forced expiration volume, from an initial measurement.

* * * * *